United States Patent
Dranoff et al.

(10) Patent No.: US 11,851,472 B2
(45) Date of Patent: Dec. 26, 2023

(54) NKG2D-IG FUSION PROTEIN FOR CANCER IMMUNOTHERAPY

(71) Applicant: Dana-Farber Cancer Institute, Inc., Boston, MA (US)

(72) Inventors: Glenn Dranoff, Sudbury, MA (US); Ryan Sullivan, Watertown, MA (US); Matthew Vanneman, Cambridge, MA (US)

(73) Assignee: Dana-Farber Cancer Institute, Inc.

(*) Notice: Subject to any disclaimer, the term of this patent is extended or adjusted under 35 U.S.C. 154(b) by 415 days.

(21) Appl. No.: 17/096,768

(22) Filed: Nov. 12, 2020

(65) Prior Publication Data

US 2021/0130434 A1 May 6, 2021

Related U.S. Application Data

(62) Division of application No. 15/775,568, filed as application No. PCT/US2016/061479 on Nov. 11, 2016, now Pat. No. 10,865,232.

(60) Provisional application No. 62/255,016, filed on Nov. 13, 2015.

(51) Int. Cl.
*A61P 35/00* (2006.01)
*A61K 45/06* (2006.01)
*C07K 14/705* (2006.01)
*A61K 38/17* (2006.01)
*A61K 38/20* (2006.01)
*C07K 14/54* (2006.01)

(52) U.S. Cl.
CPC ........ *C07K 14/7056* (2013.01); *A61K 38/178* (2013.01); *A61K 38/2086* (2013.01); *A61K 45/06* (2013.01); *A61P 35/00* (2018.01); *C07K 14/5443* (2013.01); *C07K 14/70596* (2013.01); *C07K 2319/30* (2013.01)

(58) Field of Classification Search
CPC ............ C07K 14/7056; C07K 14/5443; C07K 14/70596; C07K 2319/30; A61K 38/178; A61K 38/2086; A61K 45/06; A61K 47/6801; A61P 35/00; A61P 35/02
USPC ...................................... 424/133.1
See application file for complete search history.

(56) References Cited

U.S. PATENT DOCUMENTS

| | | | |
|---|---|---|---|
| 5,739,281 A | 4/1998 | Thøgersen et al. | |
| 6,992,174 B2 | 1/2006 | Gillies et al. | |
| 7,250,493 B2 | 7/2007 | Sun et al. | |
| 10,865,233 B2* | 12/2020 | Dranoff .............. | C07K 14/7056 |
| 2002/0009459 A1 | 1/2002 | Reed et al. | |
| 2002/0187151 A1 | 12/2002 | Raulet et al. | |
| 2008/0299137 A1 | 12/2008 | Svendsen et al. | |
| 2009/0281035 A1 | 11/2009 | Spee et al. | |
| 2010/0068137 A1 | 3/2010 | Chang et al. | |
| 2011/0177070 A1 | 7/2011 | Lofquist et al. | |
| 2011/0311535 A1 | 12/2011 | Dranoff et al. | |

FOREIGN PATENT DOCUMENTS

| | | |
|---|---|---|
| CA | 2375912 A1 | 12/2000 |
| CN | 101166755 A | 4/2008 |
| CN | 102020717 A | 4/2011 |
| EP | 2376105 A1 | 10/2011 |
| EP | 2376105 B1 | 10/2011 |
| WO | 2005/097160 A2 | 10/2005 |
| WO | 2006/107124 A | 10/2006 |
| WO | 2007/002905 A1 | 1/2007 |
| WO | 2008/036981 A1 | 3/2008 |
| WO | 2008/067305 A2 | 6/2008 |
| WO | 2010/003118 A1 | 1/2010 |
| WO | 2010/080124 A2 | 7/2010 |
| WO | 2015/036606 A1 | 3/2015 |
| WO | 2017/083612 A1 | 11/2016 |
| WO | 2017/083545 A1 | 5/2017 |

OTHER PUBLICATIONS

Extended European Search Report for EP09837720 dated Sep. 14, 2012.
International Search Report and Written Opinion for PCT/US2009/006627 dated Sep. 27, 2010.
International Preliminary Report on Patentability for PCT/US2009/006627 dated Jun. 30, 2011.
International Search Report and Written Opinion dated Feb. 1, 2017 for Application No. PCT/US2016/061479.
International Preliminary Report on Patentability dated May 24, 2018 for Application No. PCT/US2016/061479.
[No Author Listed], 2003 "Recombinant Human NKG2D/Fc Chimera. Bioscience Technology." Retrieved from <http://www.biosciencetechnology.com/articles/2003/04/recombinant-human-nkg2d-fc-chimera> on Aug. 24, 2015.
[No Author Listed], 2003 "Recombinant Human NKG2D/Fc Chimera." (New Products). HighBeam Research. Bioscience Technology. Retrieved from http://www.highbeam.com/doc/1G1-101010183. html/print on Apr. 28, 2014.
Ashkenazi et al., 1997 "Immunoadhesins as research tools and therapeutic agents." Curr Opin Immunol. 9(2):195-200.
Bell, 2008. "Natural killer cells: Dual role for NKG2D." The Signaling Gateway. Last accessed at http://www.signaling-gateway.org/update/updates/200301/nri988.html on Nov. 28, 2011. p. 1-2.
Bioscience Technology (Apr. 1, 2003).
Caillat-Zucman, 2006. "How NKG2D ligands trigger autoimmunity?" Hum Immunol. 67(3):204-7.
Carrasco et al., 2007 "The differentiation and stress response factor XBP-1 drives multiple myeloma pathogenesis." Cancer Cell. 11(4):349-60.

(Continued)

*Primary Examiner* — Yan Xiao
(74) *Attorney, Agent, or Firm* — Biospark Intellectual Property Law

(57) ABSTRACT

Methods and compositions for cancer immunotherapy are provided. The methods involve the use of a chimeric molecule (e.g., fusion protein) comprising a dimeric NKG2D portion and an Fc portion, which binds one or more NKG2D ligands. In some embodiments, the molecule further comprises a drug moiety (e.g., an IL15/Ra moiety). The methods disclosed herein are useful for the treatment of cancer that is associated with abnormal expression of one or more NKG2D ligands.

17 Claims, 13 Drawing Sheets

Specification includes a Sequence Listing.

(56) References Cited

OTHER PUBLICATIONS

Cartron et al., 2002 "Therapeutic activity of humanized anti-CD20 monoclonal antibody and polymorphism in IgG Fc receptor FcgammaRIIIa gene." Blood. 1;99(3):754-8.
Chen et al., 2013 "Fusion protein linkers: property, design and functionality." Adv Drug Deliv Rev. 65(10):1357-69. doi:10.1016/j.addr.2012.09.039.
Dietrich et al., 2012 "Peptides as Drugs: from Screening to Application" Current Pharmaceutical Biotechnology, 14(5): 1-12.
Dougan et al., 2008 "Inciting inflammation: the RAGE about tumor promotion." J Exp Med. 205(2):267-70.
Dranoff et al., 1993 "Vaccination with irradiated tumor cells engineered to secrete murine granulocyte-macrophage colony-stimulating factor stimulates potent, specific, and long-lasting anti-tumor immunity." Proc Natl Acad Sci U S A. 90(8):3539-43.
Fonseca et al., 2008 "Capitalizing on the immunogenicity of dying tumor cells." Clin Cancer Res. 14(6):1603-8.
Garrity et al., 2005 "The activating NKG2D receptor assembles in the membrane with two signaling dimers into a hexameric structure." Proc Natl Acad Sci U S A. 102(21):7641-6.
Gasser et al., 2005 "The DNA damage pathway regulates innate immune system ligands of the NKG2D receptor." Nature. 436(7054):1186-90.
GENBANK Submission; NIH/NCBI, Accession No. AAP69528.1. Rieder et al., Aug. 19, 2003.
GENBANK Submission; NIH/NCBI Accession No. AAX37025.1. Hines et al., Mar. 16, 2005.
GENBANK Submission; NIH/NCBI, Accession No. NP_031386. Liu et al., Oct. 21, 2012. 3 pages.
Gonzalez et al., 2006 "Immunobiology of human NKG2D and its ligands." Curr Top Microbiol Immunol. 298:121-38.
Guerra et al., 2008 "NKG2D-deficient mice are defective in tumor surveillance in models of spontaneous malignancy." Immunity. 28(4):571-80. Erratum in: Immunity. May 2008;28(5):723.
Hodi et al., 2008 "Immunologic and clinical effects of antibody blockade of cytotoxic T lymphocyte-associated antigen 4 in previously vaccinated cancer patients." Proc Natl Acad Sci U S A. 105(8):3005-10.
Jinushi et al., 2006 "Therapy-induced antibodies to MHC class I chain-related protein A antagonize immune suppression and stimulate antitumor cytotoxicity." Proc Natl Acad Sci U S A. 103(24):9190-5.
Jinushi et al., 2007 "Immunosurveillance: Innate and Adaptive Anti-tumor Immunity. In Cancer Immunotherapy: Immune Suppression and Tumor Growth." Eds. CG Prendergrast and EM Jaffee. Cancer Immunother. pp. 29-41.
Jinushi et al., 2007 "MFG-E8-mediated uptake of apoptotic cells by APCs links the pro- and antiinflammatory activities of GM-CSF." J Clin Invest. 117(7):1902-13.
Jinushi et al., 2008 "Enhancing the clinical activity of granulocyte-macrophage colony-stimulating factor-secreting tumor cell vaccines." Immunol Rev. 222:287-98.
Jinushi et al., 2008 "MHC class I chain-related protein A antibodies and shedding are associated with the progression of multiple myeloma." Proc Natl Acad Sci U S A. 105(4):1285-90.
Kaneko et al., 2006 "Anti-inflammatory activity of immunoglobulin G resulting from Fc sialylation." Science. 313(5787):670-3.
Kobayashi et al., 2007 "TIM-1 and TIM-4 glycoproteins bind phosphatidylserine and mediate uptake of apoptotic cells." Immunity. 27(6):927-40.
Kotturi et al., 2008 "Tumor cells expressing a fusion protein of MULT1 and Fas are rejected in vivo by apoptosis and NK cell activation." Gene Ther. 15(19):1302-10.
Lanier, 2005 "NK cell recognition." Annu Rev Immunol. 23:225-74.
Lengyel et al., 2007 "Mutations designed to destabilize the receptor-bound conformation increase MICA-NKG2D association rate and affinity." J Biol Chem. 282(42):30658-66. Epub Aug. 8, 2007.
Lin et al., 2008 "Modeling genomic diversity and tumor dependency in malignant melanoma." Cancer Res. 68(3):664-73.
Liu et al., 2008 "Engineering therapeutic monoclonal antibodies." Immunol Rev. 222:9-27.
Nimmerjahn et al., 2006 "Fcgamma receptors: old friends and new family members." Immunity. 24(1):19-28.
Nimmerjahn et al., 2007 "Antibodies, Fc receptors and cancer." Curr Opin Immunol. 19(2):239-45.
Ogasawara et al., 2005 "Function of NKG2D in natural killer cell-mediated rejection of mouse bone marrow grafts." Nat Immunol. 6(9):938-45.
Poggi et al., 2007 "NKG2D and natural cytotoxicity receptors are involved in natural killer cell interaction with self-antigen presenting cells and stromal cells." Ann N Y Acad Sci. 1109:47-57.
Polzin et al., 2000 "Involvement of ral GTP-ases in the regulation of synaptic exocytosis." Abstract-30th Annual Society for Neuroscience Meeting. 1 page.
Rowley et al., 2009 "Expression of IL-15RA or an IL-15/IL-15RA fusion on CD8+ T cells modifies adoptively transferred T-cell function in cis." Eur J Immunol. 39(2):491-506. doi: 10.1002/eji.200838594.
Strong et al., 2004 "NKG2D and Related Immunoreceptors." Adv Protein Chem. 68:281-312.
Strong, 2002 "Asymmetric ligand recognition by the activating natural killer cell receptor NKG2D, a symmetric homodimer." Mol Immunol. 38(14):1029-37.
Unni et al., 2008 "Intrinsic sensor of oncogenic transformation induces a signal for innate immunosurveillance." Proc Natl Acad Sci U S A. 105(5):1686-91.
Van Elsas et al., 1999 "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation." J Exp Med. 190(3):355-66.
Wu et al., 2014 "Targeting multiple types of tumors using NKG2D-coated iron oxide nanoparticles." Nanotechnology. 25(47):475101. doi: 10.1088/0957-4484/25/47/475101.
Yan et al., 2015 "Delivery of human NKG2D-IL-15 fusion gene by chitosan nanoparticles to enhance antitumor immunity." Biochem Biophys Res Commun. 463(3):336-43. doi: 10.1016/j.bbrc.2015.05.065.
Xia et al., 2014 "Treatment with a Fusion Protein of the Extracellular Domains of NKG2D to IL-15 Retards Colon Cancer Growth in Mice" J Immunother, 37(5): 257-258.
Zhang et al., 2005 "Alteration in the IL-2 signal peptide affects secretion of proteins in vitro and in vivo." J Gene Med. 7(3):354-65.
Zhang et al., 2006 "Generation of antitumor responses by genetic modification of primary human T cells with a chimeric NKG2D receptor." Cancer Res. 66(11):5927-33.
Zhang et al., 2012 "Immune surveillance and therapy of lymphomas driven by Epstein-Barr virus protein LMP1 in a mouse model." Cell. 148(4):739-51. doi: 10.1016/j.cell.2011.12.031.
Zhou et al., 2007 "NKG2D recognition mediates Toll-like receptor 3 signaling-induced breakdown of epithelial homeostasis in the small intestines of mice." Proc Natl Acad Sci U S A. 104(18):7512-5.
Extended European Search Report for EP1686501.2 dated Jun. 6, 2019.
Communication issued on Aug. 3, 2022 in connection with EP 16865061.2.
First Office Action dated Dec. 21, 2020 in Chinese application No. 201680071013.5 (English translation).
Bioscience Technology (Apr. 1, 2003) accessed from highbeam.com/doc/1G1-101010183.html/print.
Dietrich et al., 2013, "Peptides as Drugs: from Screening to Application," Current Pharmaceutical Biotechnology, 14(5): 1-12.
Dong et al., 1997, "Antibody Engineering," Joint Press of Beijing Medical University and Peking Union Medical College, Edition 1, pp. 92-93.
Kang et al., 2012, "Tumor-Targeted Delivery of IL-2 by NKG2D Leads to Accumulation of Antigen-Specific CD8+ T Cells in the Tumor Loci and Enhanced Anti-Tumor Effects," PLOS One 7(4): 1-9.

(56) References Cited

OTHER PUBLICATIONS

Steinbacher et al., 2014, "An Fc-optimized NKG2D-immunoglobulin G fusion protein for induction of natural killer cell reactivity against leukemia," International Journal of Cancer 136(5): 1073-1084.
Wolan et al., 2001, "Crystal Structure of the Murine NK Cell-Activating Receptor NKG2D at 1.95," Nature Immunology, 2(3): 248-254.
Xia et al., 2014, "Treatment with a Fusion Protein of the Extracellular Domains of NKG2D to IL-15 Retards Colon Cancer Growth in Mice," J Immunother, 37(5): 257-266.

\* cited by examiner

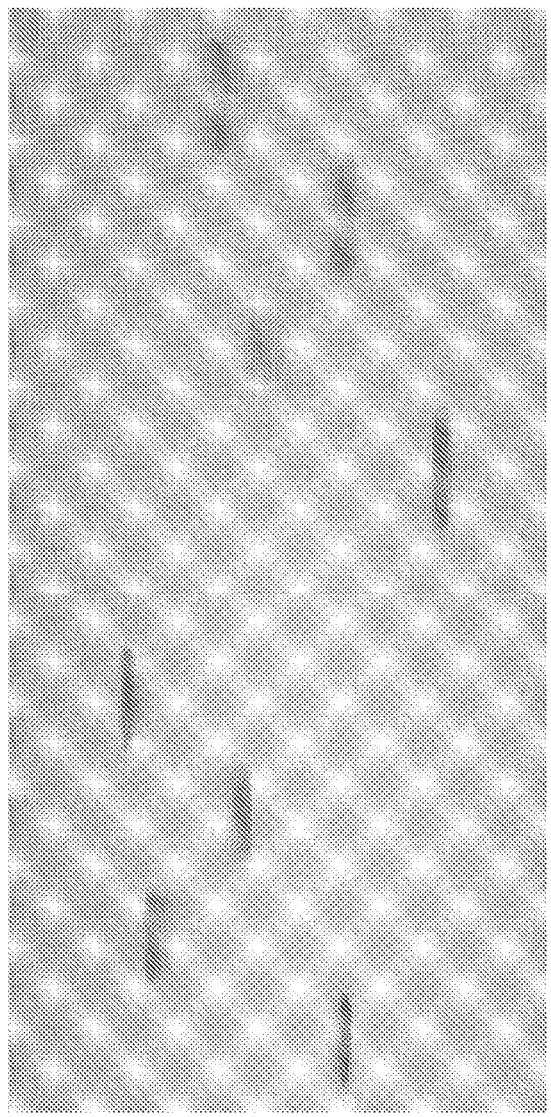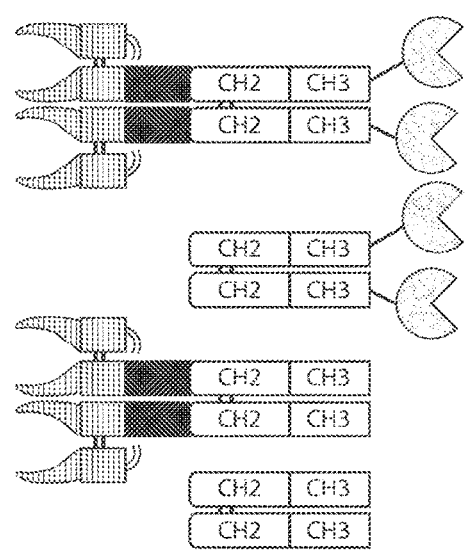
Fig. 2

FLOW CYTOMETRY ANALYSIS

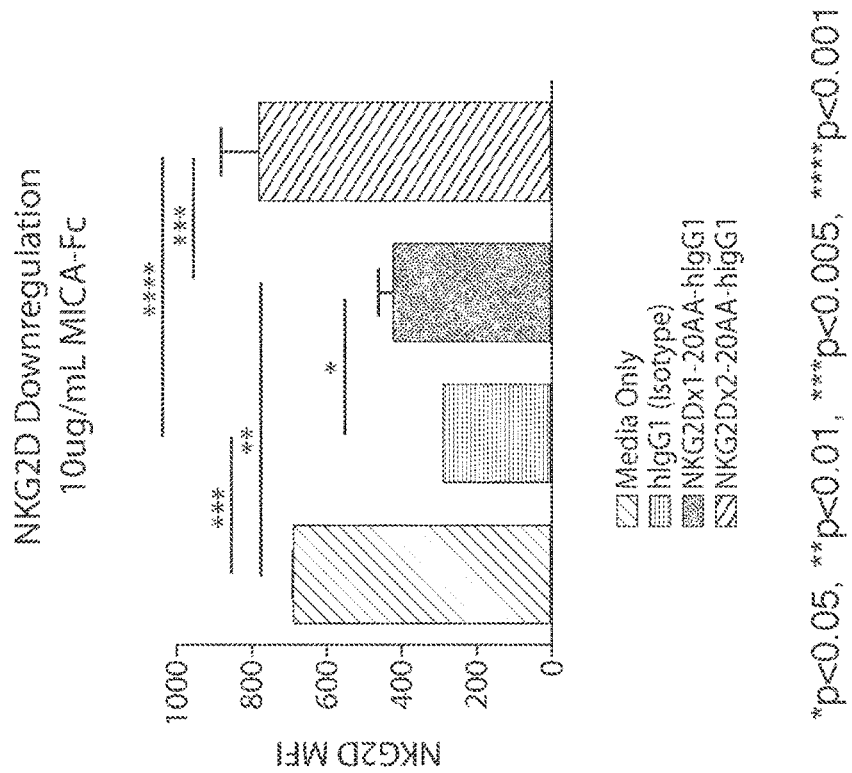
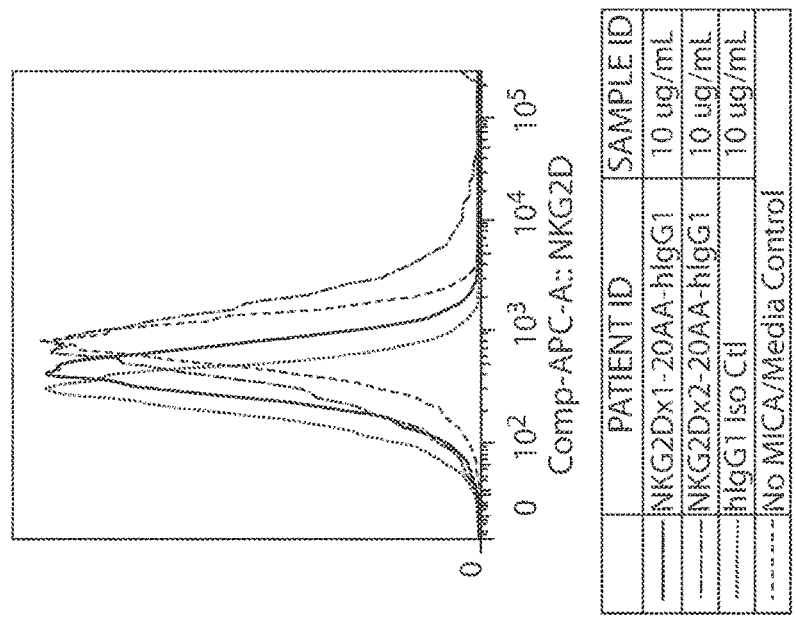
Fig. 12

SEQUENCE LISTING

```
<160> NUMBER OF SEQ ID NOS: 9

<210> SEQ ID NO 1
<211> LENGTH: 139
<212> TYPE: PRT
<213> ORGANISM: Homo sapiens

<400> SEQUENCE: 1

Phe Leu Asn Ser Leu Phe Asn Gln Glu Val Gln Ile Pro Leu Thr Glu
1               5                  10                  15

Ser Tyr Cys Gly Pro Cys Pro Lys Asn Trp Ile Cys Tyr Lys Asn Asn
            20                  25                  30

Cys Tyr Gln Phe Phe Asp Glu Ser Lys Asn Trp Tyr Glu Ser Gln Ala
        35                  40                  45

Ser Cys Met Ser Gln Asn Ala Ser Leu Leu Lys Val Tyr Ser Lys Glu
    50                  55                  60

Asp Gln Asp Leu Leu Lys Leu Val Lys Ser Tyr His Trp Met Gly Leu
```

```
                65                  70                  75                  80
Val His Ile Pro Thr Asn Gly Ser Trp Gln Trp Glu Asp Gly Ser Ile
                    85                  90                  95

Leu Ser Pro Asn Leu Leu Thr Ile Ile Glu Met Gln Lys Gly Asp Cys
            100                 105                 110

Ala Leu Tyr Ala Ser Ser Phe Lys Gly Tyr Ile Glu Asn Cys Ser Thr
        115                 120                 125

Pro Asn Thr Tyr Ile Cys Met Gln Arg Thr Val
    130                 135

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 2

Gly Gly Gly Gly Ser
1               5

<210> SEQ ID NO 3
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 3

Gly Gly Gly Gly Ser Gly Gly Gly Ser Gly Gly Gly Ser Gly
1               5                   10                  15

Gly Gly Ser
        20

<210> SEQ ID NO 4
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 4

Gly Ser Gly Ser Gly Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 5

Gly Gly Ser Gly Gly Gly Ser Gly
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 6
```

```
Gly Gly Pro Leu Gly Leu Trp Ala Gly Gly
1               5                  10
```

<210> SEQ ID NO 7
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 7

```
Ile Glu Gly Arg
1
```

<210> SEQ ID NO 8
<211> LENGTH: 77
<212> TYPE: PRT
<213> ORGANISM: Homo sapiens

<400> SEQUENCE: 8

```
Ile Thr Cys Pro Pro Met Ser Val Glu His Ala Asp Ile Trp Val
1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro
65                  70                  75
```

<210> SEQ ID NO 9
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 9

```
Asn Trp Val Asn Val Ile Ser Asp Leu Lys Lys Ile Glu Asp Leu Ile
1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

NKG2D-IG FUSION PROTEIN FOR CANCER IMMUNOTHERAPY

RELATED APPLICATIONS

This application is a division of and claims priority under 35 U.S.C. § 120 to U.S. patent application Ser. No. 15/775,568, filed May 11, 2018, now U.S. Pat. No. 10,865,232, issued Dec. 15, 2020, which is a national stage filing under 35 U.S.C. § 371 of International Application No. PCT/US2016/061479, filed Nov. 11, 2016, which claims priority under 35 U.S.C. § 119(e) to U.S. Provisional Application Ser. No. 62/255,016, filed Nov. 13, 2015, the content of each of which is incorporated herein by reference in its entirety.

BACKGROUND OF INVENTION

NKG2D is a type II transmembrane glycoprotein having an extracellular lectin-like domain. This domain lacks the recognizable calcium-binding sites found in true C-type lectins and binds protein rather than carbohydrate ligands. NKG2D is an activating receptor that is expressed in a variety of immune cells. Human NKG2D is expressed on CD8+αβ T cells, γ6 T cells, NK cells and NKT cells. In mouse systems, NKG2D also occurs on macrophages. Human ligands for NKG2D include MHC class I chain-related molecules (MICA and MICB), UL16-binding proteins (ULBP1, ULBP2, ULBP 3 and ULBP4) and RAET-1G; and mouse ligands for NKG2D include minor histocompatibility antigen 60 (H60) and retinoic acid early inducible transcript (RAE-1). Expression of NKG2D ligands also occurs in intestinal epithelial cells, tumor cells and under conditions of stress or infection.

NKG2D exists as a disulfide-linked homodimer that delivers an activating signal upon ligand binding. Signaling requires association with an adapter protein. Alternative splicing of the NKG2D mRNA results in isoforms with different cytoplasmic domains that can associate either with DAP12 to deliver a true activating signal or with DAP10 resulting in a costimulatory signal. NKG2D has been implicated in immune surveillance and immune response against viral infection. In addition, elevated levels of NKG2D ligands have been detected in proliferating cells and many types of cancer.

Certain NKG2D-Fc chimeras and their uses have been disclosed previously, for example in published PCT application WO/2010/080124, the entire content of which is incorporated herein by reference.

SUMMARY OF INVENTION

In the present disclosure, novel compositions and methods for cancer therapy are provided. The present invention is based, at least in part, on the surprising discovery that a chimeric molecule comprising two NKG2D fragments and an Fc fragment (e.g., a dimeric NKG2D-Fc chimera), which is capable of binding one or more NKG2D ligands, induces tumor cell death with improved efficacy compared to chimeric molecules comprising a single NKG2D fragment and an Fc fragment (e.g., a monomeric NKG2D-Fc chimera). In some embodiments, the dimeric NKG2D-Fc chimera described by this document binds with increased avidity to an NKG2D ligand as compared to a monomeric NKG2D-Fc chimera. In some embodiments, the avidity is increased 2-fold, 5-fold, 10-fold, 100-fold, or 1000-fold.

Accordingly, in some aspects the disclosure provides a dimeric NKG2D-Fc chimera comprising: $NKG2D_1$-$NKG2D_2$-Fc, wherein $NKG2D_1$ and $NKG2D_2$ each comprises NKG2D or a fragment thereof and can bind an NKG2D ligand; and Fc comprises a fragment crystallizable region (Fc) of an immunoglobulin. In some aspects, the disclosure provides a composition comprising the dimeric NKG2D-Fc chimera as described herein and a pharmaceutically acceptable carrier.

In some embodiments, the dimeric NKG2D-Fc chimera further comprises a drug moiety. In some embodiments, the drug moiety is attached to the amino terminus or the carboxy terminus of the chimera. In some embodiments, the drug moiety is attached to the carboxy terminus of the chimera.

In some embodiments, the dimeric NKG2D-Fc chimera further comprises at least one linking molecule, wherein the at least one linking molecule is not a contiguous portion of the $NKG2D_1$, $NKG2D_2$, Fc or drug moiety and which covalently joins: an amino acid of $NKG2D_1$ to an amino acid of $NKG2D_2$, an amino acid of $NKG2D_2$ to an amino acid of Fc, or an amino acid of Fc to the drug moiety.

In some embodiments, the at least one linking molecule is a peptide linker. In some embodiments, the peptide linker ranges from about 2 to about 25 amino acids in length. In some embodiments, the at least one linking molecule is a glycine-serine linker. In some embodiments, the glycine-serine linker is represented by the formula $(GS)_n$, wherein n is 1, 2, 3, 4, 5, 6, 7, 8, 9, 10, 11, or 12. In some embodiments, the glycine-serine linker is represented by the formula $(GGGGS)_n$ (SEQ ID NO: 2), wherein n is 1, 2, 3, 4, or 5.

In some embodiments, the chimera comprises three linking molecules, $X_1$, $X_2$ and $X_3$, wherein $X_1$ covalently joins an amino acid of $NKG2D_1$ to an amino acid of $NKGD_2$; $X_2$ covalently joins an amino acid of $NKG2D_2$ to an amino acid of Fc; and $X_3$ covalently joins an amino acid of Fc to the drug moiety. In some embodiments, $X_1$ is $(GS)_3$ (SEQ ID NO: 4) and $X_2$, $X_3$, and $X_4$ are each $(GGGGS)_4$ (SEQ ID NO: 3).

In some embodiments, the NKG2D fragment comprises an extracellular fragment of NKG2D. In some embodiments, the NKG2D extracellular fragment is represented by SEQ ID NO: 1.

In some embodiments, the Fc comprises a fragment crystallizable region (Fc) of a human immunoglobulin (IgG). In some embodiments, the human immunoglobulin is IgG1.

In some aspects, the disclosure provides a method for treating cancer comprising administering to a subject having an NKG2D ligand expressing cancer a dimeric NKG2D-Fc chimera as described by this document in an amount effective to treat the cancer.

In some embodiments, the NKG2D ligand expressing cancer is melanoma, lung cancer, plasma cell cancer, leukemia, lymphoma, ovarian cancer, colon cancer, pancreatic cancer or prostate cancer. In some circumstances, one or more of these cancers may be present in a subject.

In some embodiments, the method further comprises treating the subject with an additional anti-cancer therapy. In some embodiments, the additional anti-cancer therapy is selected from the group consisting of surgery, radiation therapy, chemotherapy, gene therapy, DNA therapy, viral therapy, RNA therapy, adjuvant therapy, and immunotherapy.

In some embodiments, the additional cancer therapy is a chemotherapy that damages DNA.

In some embodiments, the NKG2D ligand is MICA, MICB, ULBP1, ULBP2, ULBP3, ULBP4, ULBP5, or ULBP6.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

FIG. 2 shows that hNKG2Dx2-hIgG1-hIL15/Ra is produced as a single fusion protein, and is purified by protein A.

FIG. 12 shows NKG2Dx2-hIgG1 neutralization of soluble MICA is superior to NKG2Dx1-hIgG1. * depicts $p<0.05$,  depicts $p<0.01$, * depicts $p<0.005$, and **** depicts $p<0.001$.

DETAILED DESCRIPTION OF INVENTION

Figure 1:
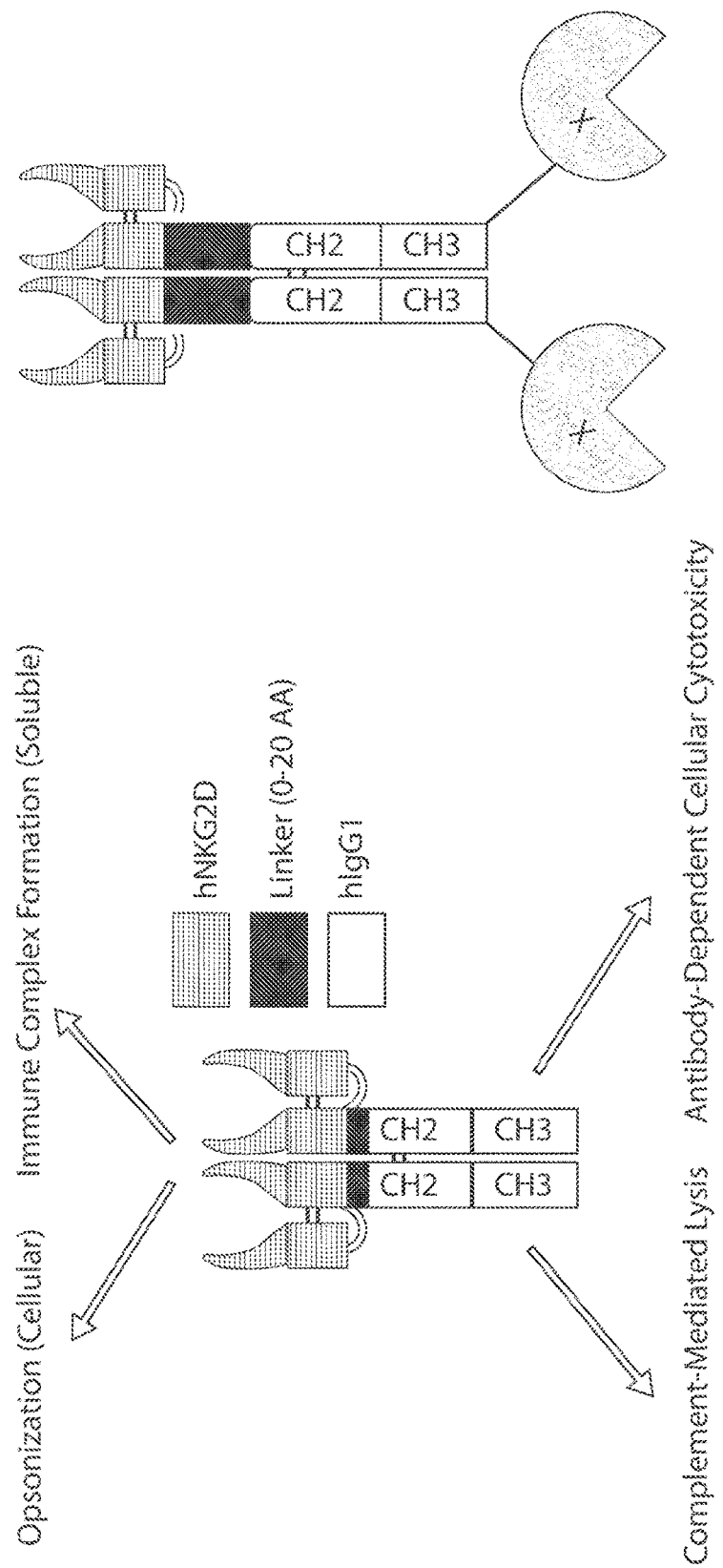
FIG. 1 shows a diagram of dimeric NKG2D-Fc chimeras with (right) and without (left) a drug moiety.

Disclosed herein are novel compositions and methods for cancer immunotherapy. Compositions and methods of the present invention are based, at least in part, on the surprising discovery that a chimeric molecule comprising two NKG2D fragments and an Fc fragment (e.g., a dimeric NKG2D-Fc chimera), which is capable of binding one or more NKG2D ligands, induces tumor cell death with improved efficacy compared to chimeric molecules comprising a single NKG2D fragment and an Fc fragment (e.g., a monomeric NKG2D-Fc chimera).

Monomeric NKG2D-Fc chimeras described in the prior art (e.g., constructs described in published PCT application WO/2010/080124), exhibit a low binding avidity to NKG2D ligands (e.g., a low binding avidity index). The dimeric NKG2D-Fc constructs described herein provide increased binding avidity (e.g., an improved avidity index of at least 1.1, 2, 3, 4, 5, 6, 7, 8, 9, 10 or more) compared to the prior art monomeric constructs by providing multiple NKG2D receptors (or portions thereof) on the same molecule. Without wishing to be bound by any particular theory, the presence of multiple NKG2D receptors on a single molecule is thought to increase the number and duration of NKG2D-NKG2D ligand binding interactions, leading to increased anti-tumor activity. Indeed, as shown in the Examples section, dimeric NKG2D-Fc chimeras exhibit up to 100-fold improved binding avidity compared to the prior art monomeric NKG2D-Fc chimeras. However, the success of this approach was not predictable because it was not known whether increasing the number of receptors (or portions thereof) in the chimeric construct would inhibit binding interactions (e.g., via steric hindrance), or cause aggregation of the chimeras that could interfere with the stability of the molecule.

NKG2D ligand(s) are known to be expressed on cancer cells. Therefore, in some embodiments, the disclosure provides methods for cancer therapy in a subject (e.g., a human subject), the method comprising administering to a subject having an NKG2D ligand-expressing cancer a dimeric NKG2D-Fc chimera as described herein. Unlike an immunotherapy that employs a monoclonal antibody against an NKG2D ligand, such as MICA, the methods provided herein are believed to have broad effects against cancer, on the basis that NKG2D binds to multiple ligands.

The dimeric NKG2D-Fc chimera can target any or all NKG2D ligands that are expressed on human tumor cells, and thus is capable of mediating tumor cell destruction through complement lysis and ADCC. The NKG2D-Fc chimera is also capable of opsonizing any tumor cells that express at least one NKG2D ligand. The NKG2D-Fc chimera can promote efficient cross-presentation (e.g., priming) by dendritic cells, leading to the induction of potent T cell responses against the tumor. Moreover, this chimera is capable of binding and sequestering any "shed" (e.g., soluble or released) NKG2D ligand(s) produced by tumor cells, thereby alleviating immune suppression due to down-regulation of NKG2D expression in response to tumor-derived soluble ligands.

NKG2D-Fc

In some aspects the disclosure provides a dimeric NKG2D-Fc chimera comprising: NKG2D$_1$-NKG2D$_2$-Fc, wherein NKG2D$_1$ and NKG2D$_2$ each comprises NKG2D or a fragment thereof and can bind an NKG2D ligand; and Fc comprises a fragment crystallizable region (Fc) of an immunoglobulin. In some embodiments, the NKG2D fragment comprises an extracellular fragment of NKG2D. In some embodiments, the NKG2D extracellular fragment is represented by SEQ ID NO: 1.

As used herein, a "dimeric NKG2D-Fc chimera" is a chimeric molecule comprising two NKG2D ligand binding sites, wherein each ligand binding site comprises at least a portion or all of the NKG2D receptor and is capable of binding an NKG2D ligand. The ligand binding sites are fused to an Fc fragment. In the Examples section and the Figures, the two NKG2D ligand binding sites of dimeric NKG2D-Fc chimera are also referred to collectively as "NKG2Dx2". The monomeric NKG2D-Fc chimera described in the prior art can be referred to as "NKG2Dx1". The terms "chimera," "chimeric molecule," and the like generally refer to a molecule that is comprised of parts that are from multiple origins or sources. In some embodiments, dimeric NKG2D-Fc is produced as a recombinant chimeric fusion protein.

In some embodiments, the dimeric NKG2D-Fc chimera described herein binds with increased avidity to an NKG2D ligand as compared to a monomeric NKG2D-Fc chimera. As used herein, "avidity" refers to overall strength across multiple affinities of individual non-covalent binding interactions between a ligand and a receptor. Methods of measuring binding avidity are known in the art and include, for example, ELISA, surface plasmon resonance analysis, CD analysis, fluorescence quenching, size-exclusion binding assay and isothermal titration calorimetry. For brief descriptions of these assays, see, for example, Lengyel et al., 2007, J. Biol. Chem., 282: 30658-666). In some embodiments, binding avidity is determined by measuring avidity index. In some embodiments, the binding avidity of the dimeric NKG2D-Fc chimera to a NKG2D ligand is increased between about 2-fold and about 2000-fold as compared to the monomeric NKG2D-Fc chimera. In some embodiments, the binding avidity is increased between about 2-fold and 1000-fold. In some embodiments, the binding avidity is increased between about 2-fold and 100-fold. In some embodiments, the binding avidity is increased between about 5-fold and 1000-fold. In some embodiments, the binding avidity is increased between about 5-fold and 200-fold. In some embodiments, the binding avidity is increased between about 2-fold and about 20-fold. In some embodiments, the binding avidity is increased 2-fold, 5-fold, 10-fold, 100-fold, or 1000-fold. In some embodiments, the binding avidity is increased at least 2-fold, at least 5-fold, at least 10-fold, at least 100-fold, or at least 1000-fold. In some embodiments, the dimeric NKG2D-Fc constructs has an increased binding avidity index as compared to the monomeric NKG2D-Fc chimera, e.g., an improved avidity index of at least 1.1, 2, 3, 4, 5, 6, 7, 8, 9, 10 or more.

NKG2D

In some aspects the disclosure provides a dimeric NKG2D-Fc chimera comprising: two NKG2D or fragments thereof. NKG2D, also referred to as KLRK1; killer cell lectin-like receptor subfamily K, member 1; CD314; KLR; NKG2-D; FLJ17759; F1175772 or D12S2489E, is one of the major triggering receptors of NK cells and is well known in the art. See, for example, Garrity et al. (2005). The portion of the NKG2D receptor used for dimeric NKG2D-Fc is based on the known sequences of NKG2D (e.g., Accession: NP_031386) or derivatives thereof that bind at least one ligand. Derivatives of NKG2D that can be used in the compositions and methods of the invention include, but are not limited to, NKG2D sequences containing one or more mutations, such as a point mutation, a substitution, a deletion mutation and/or an insertion mutation. One of ordinary skill in the art can readily determine suitable derivatives of NKG2D according to the teaching of the present disclosure and knowledge available in the art. At the cDNA level, such a mutation may be a silent mutation. Alternatively, the mutation may result in a change in the corresponding amino acid residue. Where the latter is the case, the change may constitute a conservative change, such that an amino acid residue is replaced with another amino acid residue of similar characteristics. In some cases, however, a mutation may result in a substitution that is non-conservative. Such mutations are acceptable to the extent that the dimeric NKG2D-Fc chimera is capable of binding to an NKG2D ligand.

In some embodiments, each NKG2D portion of a dimeric NKG2D-Fc chimera is a full length NKG2D polypeptide. The full length sequence of NKG2D has been described in the literature. See, for example, RefSeq Accession: NP_031386. Additionally, alternative splice variants of NKG2D have been described. For purposes of the instant invention, any one of such alternatively spliced variants may be used, provided that the resulting polypeptide, when constructed as a dimeric NKG2D-Fc chimera, is capable of binding its ligand(s).

In some embodiments, each NKG2D portion of a dimeric NKG2D-Fc chimera is a partial sequence (i.e., fragment) of the NKG2D receptor polypeptide, provided that the resulting polypeptide, when constructed as a dimeric NKG2D-Fc chimera, retains the ability to bind its ligand(s). For example, each NKG2D portion of the dimeric NKG2D-Fc construct may be shortened by either end of the NKG2D sequence by one or more amino acid residues. More specifically, the N-terminus of the NKG2D sequence may be deleted by 1, 2, 3, 4, 5, 6, 7, 8, 9, 10, 11, 12, 13, 14, 15, 16, 17, 18, 19, 20, about 30, about 40, about 50, about 60, about 70, about 80 or more residues. Similarly, the C-terminus of the NKG2D sequence may be deleted by 1, 2, 3, 4, 5, 6, 7, 8, 9, 10, 11, 12, 13, 14, 15, 16, 17, 18, 19, 20 or more residues. In some embodiments, both the N-terminus and the C-terminus may be shortened as described.

It has been shown that the extracellular portion of NKG2D contributes to the formation of homodimers and forms a ligand-binding site(s). Thus, it is possible to delete part or all of the intracellular portion of NKG2D and still maintain the ability to bind its ligand(s). For example, the dimeric NKG2D-Fc chimera described in this disclosure may contain predominantly an extracellular fragment of the NKG2D receptor. Structural analyses have revealed that amino acid residues 78 to 216 of the human NKG2D sequence correspond to the extracellular portion of the NKG2D, containing ligand-binding sites. For a murine counterpart, the extracellular domain is amino acid residues 78-232, 94-232 or 92-232.

Accordingly, in some embodiments, each NKG2D of the dimeric NKG2D-Fc construct comprises the extracellular portion of the NKG2D sequence, e.g., amino acid residues 78-216 of human NKG2D; 78-232, 94-232 or 92-232 of murine NKG2D. In some embodiments, a dimeric NKG2D-Fc construct comprises a portion of the extracellular domain. Thus, the extracellular domain of the dimeric NKG2D-Fc construct may be shortened at the N-terminus, at the C-terminus, or both. For example, the N-terminus of the extracellular domain used to generate a dimeric NKG2D-Fc may be shortened by one or more amino acid residues, e.g., 1, 2, 3, 4, 5, 6, 7, 8, 9, 10, 11, 12, 13, 14, 15, 16, 17, 18, 19, 20, about 30, about 40, about 50, about 60, and so forth, relative to the full extracellular portion of the polypeptide. The C-terminus of the extracellular domain used to generate an NKG2D-Fc may be shortened by one or more amino acid residues, e.g., 1, 2, 3, 4, 5, 6, 7, 8, 9, 10, 11, 12, 13, 14, 15, 16, 17, 18, 19, 20, about 30, about 40, about 50, about 60, and so forth, relative to the full extracellular portion of the polypeptide. Using a human NKG2D as an example, the dimeric NKG2D-Fc construct may contain a fragment of the extracellular domain, wherein the N-terminus of the domain begins at amino acid residue 79, 80, 81, 90, 91, 92, 93, 94, 95, 96, 97, 98, 99, 100, about 110, about 120, about 130, about 140 or about 150. Similarly, the dimeric NKG2D-Fc construct may contain a fragment of the extracellular domain, wherein the C-terminus of the domain ends at amino acid residue 231, 230, 229, 228, 227, 226, 225, 224, 223, 222, 221, 220, 219, 218, 217, 216, 215, 214, 213, 212, 211, 210, 209, 208, 207, 206, 205, and so forth. Such deletions at each end of the extracellular domain of the NKG2D sequence may be combined.

The skilled artisan recognizes that dimeric NKG2D-Fc chimera described by the disclosure may comprise two of the same NKG2D fragments or two different NKG2D fragments. For example, in some embodiments, a dimeric NKG2D-Fc chimera comprises two NKG2D fragments corresponding to amino acid residues 78 to 216 of the human NKG2D. In some other embodiments, a dimeric NKG2D-Fc chimera comprises two NKG2D fragments, where the first fragment corresponds to amino acid residues 78 to 216 of the human NKG2D and the second fragment corresponds to a different portion of the NKG2D extracellular domain (e.g., amino acid positions 140 to 210 of the human NKG2D).

Also contemplated are dimeric NKG2D-Fc derivatives that include one or more mutations in the NKG2D portion of the construct at the interface of the NKG2D-ligand binding. In particular, certain mutations are known to affect the binding affinity between the NKG2D receptor and its ligand (e.g., MICA). See, for example, Lengyel et al., 2007, J. Biol. Chem., 282: 30658-666. The three dimensional structure of a complex between NKG2D and MICA has been described. Accordingly, one of ordinary skill in the art may determine the amino acid residues of NKG2D that contribute to the interaction with its ligand and test the effect of mutations by systematically altering the key residues. In any of the embodiments, the resulting dimeric NKG2D-Fc chimera is capable of binding ligand(s). For a comprehensive review of the amino acid residues that are involved in receptor-ligand contact, see, for example, Strong and McFarland, 2004, Advances in Protein Chemistry, 68: 281-213. According to published studies, key residues that are thought to be important in the interaction with the ligand have been mapped to amino acid residues approximately from 150 to 207 in human NKG2D, which correspond to residues approximately from 166 to 223 in mouse NKG2D. Therefore, each NKG2D fragment of the dimeric NKG2D-Fc construct of the invention preferably comprises a fragment spanning at least most of these residues (e.g., residues 150 to 207 in human NKG2D). Likewise, it will be understood that conservative substitutions, deletions or mutations outside these regions can potentially be tolerated with ease in many instances.

Some amino acid residues have been identified to be especially important for mediating ligand binding. Specifically, residues of human NKG2D important for binding to MICA include Y152, Q185, K197, Y199, E201 and N207. Residues of human NKG2D important for binding to ULBP3 include I182, Y199 and Y152. Residues of murine NKG2D important for binding to RAE-1β include K166, Y168, Y215, K213, E217 and N223. In preferred embodiments, therefore, most or all of these residues (of a corresponding dimeric NKG2D construct) are maintained without a mutation or deletion at the position where broad permissibility (e.g., specificity) for multiple ligands is desirable. However, it is also possible to design a dimeric NKG2D-Fc construct that preferentially binds one ligand over another ligand by strategically introducing a mutation at one or more of these key residues that confer selective ligand-recognition and binding. On the other hand, certain amino acid residues are involved in the binding of various ligands. For example, Y152 and Y199 in human NKG2D, which are equivalent to Y168 and Y215 respectively in the murine counterpart, contribute to the binding of MICA as well as ULBP3. Therefore, in some embodiments, these residues are unmodified so as to retain broad ligand specificity.

The Examples provided below present a representative dimeric NKG2D-Fc chimera, wherein each NKG2D fragment corresponds to amino acid residues 78 to 216 of the human NKG2D. However, it should be appreciated that the same approach may be employed for NKG2D sequences derived from any other species that are known to develop cancer. For example, the NKG2D fragment of dimeric NKG2D-Fc may have 1, 2, 3, 4, 5, 6, 7, 8, 9, 10 or more amino acid changes, such as deletions, insertions and substitutions, as long as the dimeric NKG2D-Fc retains its ligand binding activity.

The present invention includes variants of dimeric NKG2D-Fc constructs that contain one or more amino acid changes as described above, to the extent that the dimeric NKG2D-Fc chimera binds to its native ligand or ligands. To determine whether a dimeric NKG2D-Fc variant containing a particular mutation retains ligand binding activity, binding assays can be carried out, in which binding affinity and/or binding capacity of the particular dimeric NKG2D-Fc chimera to its ligand(s) may be evaluated. A number of methods are known in the art by which receptor-ligand interactions may be measured. These methods for assaying ligand binding include, without limitation, ELISA, surface plasmon resonance analysis, CD analysis, fluorescence quenching, size-exclusion binding assay and isothermal titration calorimetry. For brief descriptions of these assays, see, for example, Lengyel et al. (2007).

Fc Fragment

In some embodiments, a dimeric NKG2D-Fc chimera comprises a fragment crystallizable region (Fc) of an immunoglobulin. The Fc region of immunoglobulins plays a significant role in mediating immune defense. FcγRs are widely expressed as transmembrane glycoproteins on a number of cell types, including macrophages, NK cells, dendritic cells, B cells, neutrophils and mast cells. Fc-mediated activities include recruitment of effector cells via Fc-FcγR interactions. There are two classes of Fc receptors that can be distinguished functionally: the activating Fc receptor class and the inhibitory Fc receptor class. Activating Fc receptors include human FcγRIA, FcγRIIA and FcγRIIIA, as well as their murine orthologues, i.e., FcγRI, FcγRIII FcγRIV. Activating FcγRs mediate ADCC and ADCP, induce endocytosis of immune complexes leading to antigen presentation, and contribute to the production and release of cytokines and proinflammatory factors. For general review of the IgG structure and mechanisms of action, see Liu et al. (2008; Immunological Reviews, 222: 9-27). As described in more detail herein, the Fc portion of dimeric NKG2D-Fc is a domain that binds an activating Fc receptor, and preferably an activating Fc Ig domain and includes the hinge region that allows for dimerization.

The Fc portion of the dimeric NKG2D chimera useful for this disclosure can be readily adapted to render it species-specific. For use in a murine system, e.g., cells derived from a mouse, the Fc fragment used to generate dimeric NKG2D-Fc is preferably that of a murine origin. In some embodiments, an Fc fragment of the murine IgG2a is preferred.

For use in a human subject, e.g., for cancer treatment, the Fc fragment used to generate dimeric NKG2D-Fc is preferably that of a human origin. In particularly preferred embodiments, NKG2D-Fc comprises an activating Fc Ig domain. Among the four human IgG isotypes, an activating Fc domain of IgG1 is preferred for the preparation of dimeric NKG2D-Fc. Thus, in some embodiments, the Fc comprises a fragment crystallizable region (Fc) of a human immunoglobulin (IgG). In some embodiments, the human immunoglobulin is IgG1. Experimental data relating to chimeric constructs containing an Fc region of the human IgG1 are provided in the Examples section.

The art appreciates that different antibody isotypes have a varying degree of cytotoxic potential in vivo (See, for example, Nimmerjahn F. & Ravetch J V., 2006, Immunity, 24:19-28). For example, the murine IgG2a and IgG2b isotypes are more efficient in clearing infections such as bacterial infections and viral infections and in killing tumor cells than their IgG1 or IgG3 counterparts. This is attributable at least in part to differential ratios of activating versus inhibitory FcRs present in vivo. Similarly, with respect to human IgG isotypes, IgG1 and IgG3 have a stronger interaction with FcRs than IgG2 or IgG4. Moreover, certain polymorphic allotypes of a given isotype may influence affinity for an Fc receptor. Indeed, there are allelic variants of activating FcRs that will significantly affect the affinity for certain antibody isotypes. For example, the FcγRIIIa receptor 158V allotype displays a higher affinity for human IgG1 and increased antibody-dependent cellular cytotoxicity (Cartron G. et al., 2002, Blood, 99: 754-758).

Without wishing to be bound by any particular theory, it is possible to optimize the interaction between the Fc portion of the dimeric NKG2D-Fc chimera to its corresponding Fc receptor by strategically selecting or modifying the Fc allele used for preparing the dimeric NKG2D-Fc chimera. Accordingly, the invention contemplates using a mutant or an allotype of an Fc fragment. A number of useful mutations within an Fc domain have been described, which can affect the interaction of an Fc and its receptor, the effector function of the Fc, as well as the half-life of the Fc-containing molecule. These include specific amino acid substitutions and/or modifications to carbohydrate moieties in the Fc. For review, see, for example, Liu et al., 2008, Immunological Reviews, 222:9-27; Nimmerjahn & Ravetch, 2007, Curr. Opin. Immunol., 19(2): 239-45.

The structure of Fc fragments generally is known in the art. Briefly, the Fc region of a typical IgG molecule is a symmetric homodimer of the carboxy-terminal portion of heavy chains and is composed of the $C_H2$ and $C_H3$ domains, which are separated from the Fab by a flexible hinge region. The Fc region is stabilized by non-covalent interactions between domains. The Fc region interacts with FcRs to exert effector functions or to regulate the catabolism of IgG. The heavy constant regions (Cγ2 and Cγ3) and the hinge region located between the variable domain and the constant regions interact with C1q and Fc receptors (FcRs). Thus, the heavy constant regions of the IgG molecule are responsible for its effector functions, since they include binding sites for complement and for FcRs on different effector cells. Recruitment of effector cells is therefore mediated via the Fc-FcγR interactions.

In general, the interaction of an antibody with complement initiates complement-dependent cytotoxicity (CDC), and FcγR interactions mediate antibody-dependent cell toxicity (ADCC) and antibody-dependent cell phagocytosis (ADCP). The classical activation pathway of CDC is triggered when C1, the first component of the pathway, binds to the hinge-Fc portion of the IgG in an antigen-antibody complex. Subsequent activation of the complement cascades eventually induces the formation of a C5-C9 membrane attack complex that leads to the death of the target cell. ADCC, on the other hand, is dependent upon the ability of the FcγR-bearing cells of the innate immune system (e.g., NK cells, monocytes, macrophages and granulocytes) to recognize the Fc domain of antibody bound to target cells. This recognition triggers effector cells to release cytoplasmic perforin, granulysin, and granzymes that induce apoptosis and lysis of target cells. The major effector cells in ADCC are NK cells, which express the type of FcγRs that recognize the IgG1 and IgG3 subclasses and trigger cytotoxic effects in vivo.

In the context of the present invention, as demonstrated in the Examples, the dimeric NKG2D-Fc chimeras described herein are capable of mediating equivalent cellular effects by virtue of having a functional Fc portion, coupled with the dimeric NKG2D portion that can broadly but specifically recognize and bind to its ligands.

As noted, there are activating receptors (FcγRI, FcγRIIA and FcγRIII) and inhibitory (FcγRIIB) receptors. In general, interaction of IgGs with activating FcγRs triggers cell activation, while interaction with FcγRIIB inhibits cell activation. With the exception of B cells and NK cells, activating and inhibitory FcγRs are co-expressed on the same effector cells, thereby generating a threshold for cell activation. B cells express only the inhibitory FcγRIIB and therefore cannot be activated by endogenous IgG under physiological conditions. NK cells express the activating FcγRIII so that they can kill target cells independently of pre-activation (or priming).

FcγRIIA and FcγRIII (CD16) have low affinities for monomeric IgG and are thought to be critical for triggering effector functions, leading to anti-tumor activity. Thus, it is possible to design a dimeric NKG2D-Fc such that it is genetically engineered to have increased affinities for the activating FcγRIII, and decreased affinities for the inhibitory FcγRIIB Accordingly, the amino acid residues of dimeric NKG2D-Fc molecules that contribute to their direct interaction with FcγRs, which are located primarily in the lower hinge region and are adjacent to the Cγ2 region, may be modified, and such variants are embraced by this invention. It has been shown that the region corresponding to amino acid residues 234-237 of the IgG is required for binding to FcγRs. In addition, other residues that are important in IgG-FcγRs interactions have been shown to be located in the Cγ2 domain and include Asp265, Asp270, Ala327, Pro329 and Lys338.

Several strategies are contemplated to generate dimeric NKG2D-Fc chimeras with enhanced activities. To engineer the dimeric NKG2D-Fc with an enhanced ADCC capability, at least two approaches are contemplated. First, based on the amino acid residues in an IgG1 that were identified to be critical for its binding to activating and inhibitory FcγRs, the invention provides variants of dimeric NKG2D-Fc chimeras that enhance or reduce, respectively, the affinity for these receptors. Accordingly, in one embodiment, the triple amino acid substitution, Ser298Ala/Glu333Ala/Lys334Ala, where the position of each residue is based on IgG1, is provided. The dimeric NKG2D-Fc containing this triple mutation should exhibit a higher affinity for FcγRIIIA but not for FcγRIIB, thereby promoting ADCC. Similarly, in another embodiment, the dimeric NKG2D-Fc variant contains the double mutation in the Fc, Ser239Asp/Ile332Glu, which is expected to exert improved ADCC. Other mutations for enhancing ADCC include, without limitation, Ser239Asp/Ala330Leu/Ile332Glu and Ser239Asp/Ser298Ala/Ile332Ala. Similarly, in some embodiments, mutations that combine increased binding to FcγRIIIA (e.g., activating receptors) and reduced binding to FcγRIIB are contemplated. Examples of such Fc mutations include Phe243Leu/Arg292Pro/Tyr300Leu/Val305Ile/Pro396Leu, without limitation (the positions of the residues are based on IgG1).

The second approach relates to modifying the carbohydrate moieties in the Fc based on the observation that some modifications significantly affect the affinity of the Fc for FcγRs. It has been shown that the Fc domain contains two asparagine N-linked oligosaccharide sites (reviewed in Liu et al., 2008). ADCC requires the presence of certain oligosaccharides and is dependent upon changes in the structure of the oligosaccharides. In particular, previous studies have shown that removing the fucose moiety attached to the innermost GlcNAc of the biantennary complex-type oligosaccharides dramatically increases ADCC by improving the binding of the Fc to FcγRIIIA without impairing CDC activity. Based on this observation, in one embodiment, the invention provides fucose-deficient dimeric NKG2D-Fc. In some embodiments, the chimera completely lacks the fucose moiety (i.e., non-fucosylated). In other embodiments, the chimera is hypofucosylated.

To make dimeric NKG2D-Fc containing modified carbohydrates, host cells may be engineered to express the enzymes that catalyze the desired modification(s). For example, host cells, such as Chinese hamster ovary (CHO) cells may be transfected with the enzyme, β-(1,4)-N-acetylglucosaminyltransferase III (GnT-III), which elevates the level of bisected, non-fucosylated oligosaccharides. The NKG2D-Fc product generated from these host cells can have a dramatically enhanced ADCC activity. In addition, in some embodiments, the content of fucose in NKG2D-Fc may be manipulated by α-1,6-fucosyltranferase (FUT8)-knockout cells lacking core-fucosyl transferase activity. Alternatively, small interfering RNA may be used to constitutively inhibit the expression of the FUT8 enzyme to achieve the same effect. In some embodiments, host cells deficient in guanosine diphosphate (GDP)-mannose 4,6-dehydratase (GMD) may be used to yield non-fucosylated NKG2D-Fc.

Next, to engineer the dimeric NKG2D-Fc with an enhanced complement activity, various mutations in the Fc domain are contemplated. Generally, complement can be activated by at least three pathways, leading to the formation of the membrane attach complex C5b-9, which forms pores in the plasma membranes of target cells and causes their lysis. C1q binding to the Fc domain is a critical step in this process. Among the human IgG subclasses, only IgG1 and IgG3 can initiate the complement cascade. In some embodiments, mutations are introduced to the Fc domain of the dimeric NKG2D-Fc, so as to promote C1q recruitment and the C1q-Fc interaction. The residues of the Fc targeted for such mutations include, but are not limited to: Asp270, Lys322, Pro329 and Pro331. These mutations involve substituting the corresponding residue(s) with nonpolar neutral amino acids, such as Ala, Met, or Trp. In a specific embodiment, the dimeric NKG2D-Fc contains the mutation, Lys326Trp, Clu333Ser or both.

To achieve increased C1q binding and enhanced CDC, some embodiments of the invention involve introducing a mutation or mutations to certain residues of the hinge region of human IgG1. Non-limiting examples of such mutations include: Lys222Trp/Thr223Trp, Cys220Asp/Asp221Cys, Cys220Asp/Asp221Cys/Lys222Trp/Thr223Trp, Lys222Trp/Thr223Trp/His224Trp and Asp221Trp/Lys222Trp.

In addition, it should be noted that when fusion proteins with artificial sequences and activities are used as therapeutic agents, in some circumstances, patients treated with such a fusion protein trigger an unwanted immune response, such as development of antibodies against the agent. Certain structural modifications of an Fc fragment have been shown to reduce immunogenicity of a therapeutic fusion protein. See, for example, U.S. Pat. No. 6,992,174 B2 by Gillies et al., which is incorporated by reference herein; Liu et al., 2008, Immunological Reviews, 222:9-27. Such modifications may be useful for an effective design of dimeric NKG2D-Fc described in the present disclosure.

Linkers

The dimeric NKG2D-Fc construct used in the methods of the present disclosure may further comprise at least one linking moiety that connects a first NKG2D portion (e.g., $NKG2D_1$) with a second NKG2D portion (e.g., $NKG2D_2$), an NKG2D portion (e.g., $NKG2D_1$ or $NKG2D_2$) with an Fc fragment, and/or an Fc fragment to a drug moiety. In some embodiments, a linking moiety (e.g., linking molecule) is referred to as $X_1$, $X_2$, or $X_3$. In some cases, a hinge region of Fc fusion protein molecules serves as a spacer between the Fc region and the fused peptide (e.g., soluble receptor), allowing these two parts of the molecule to function separately (see, for example, Ashkenazi et al., 1997).

In some embodiments, the at least one linking moiety (e.g., linking molecule) is not a contiguous portion of the $NKG2D_1$, $NKG2D_2$, Fc, or drug moiety and covalently joins: an amino acid of $NKG2D_1$ to an amino acid of $NKG2D_2$, an amino acid of $NKG2D_2$ to an amino acid of Fc, or an amino acid of Fc to the drug moiety. As used herein, a linking molecule that is "not a contiguous portion" means that the each NKG2D portion (e.g., $NKG2D_1$ and $NKG2D_2$), a NKG2D portion and the Fc portion, and/or the Fc portion and a drug moiety of the chimera are connected via an additional element that is not a part of the NKG2D or immunoglobulin or drug moiety, that is contiguous in nature with the portions of the chimera that it joins, and functions as a linker. Non-limiting examples of a linking molecule that is not a contiguous portion of either NKG2D, Fc, or drug moiety are described below.

The linking molecule may be a peptide linker. In some embodiments, the peptide linker ranges from about 2 to about 25 amino acids in length. In some embodiments, the peptide linker is 20 amino acids in length. In some embodiments, the peptide linker ranges from about 4 to about 16 amino acids in length. In some embodiments, the peptide linker is 2, 3, 4, 5, 6, 7, 8, 9, 10, 11, 12, 13, 14, 15, 16, 17, 18, 19, 20, 21, 22, 23, 24, or 25 amino acids in length. In some embodiments, the peptide linker is longer than 25 amino acids in length. Where the linker is a peptide linker, the dimeric NKG2D-Fc chimera may be produced as a single recombinant polypeptide using a conventional molecular biological/recombinant DNA method.

In some embodiments, a peptide linker provides a protease-dependent cleavable site. Examples of protease-cleavable peptide linkers include, without limitation, the MMP sensitive linker GGPLGLWAGG (SEQ ID NO: 6) and the factor Xa-sensitive linker IEGR (SEQ ID NO: 7). The art is familiar with a variety of cleavable sequences that may be employed for the methods provided herein, for example those disclosed in Chen et al., Adv. Drug Deliv. Rev. (2013), 65(10): 1357-69).

In some embodiments of the present invention, a flexible peptide linker is used. A flexible peptide linker is preferably about 25 or fewer amino acids in length. In some embodiments, a flexible peptide linker is 20 amino acids in length. In some embodiments, a peptide linker contains about 20 or fewer amino acid residues, e.g., 2, 3, 4, 5, 6, 7, 8, 9, 10, 11, 12, 13, 14, 15, 16, 17, 18, 19, and 20. In some embodiments, a peptide linker contains about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine. In some embodiments, the flexible peptide linker is a glycine-serine linker.

In some embodiments, the glycine-serine linker is represented by the formula $(GS)_n$, wherein n is 1, 2, 3, 4, 5, 6, 7, 8, 9, 10, 11, or 12. In some embodiments, the glycine-serine linker is represented by the formula $(GGGGS)_n$ (SEQ ID NO: 2), wherein n is 1, 2, 3, 4, or 5.

In some embodiments, a dimeric NKG2D-Fc chimera comprises three linking molecules, $X_1$, $X_2$ and $X_3$, wherein $X_1$ covalently joins an amino acid of $NKG2D_1$ to an amino acid of $NKGD_2$; $X_2$ covalently joins an amino acid of $NKG2D_2$ to an amino acid of Fc; and $X_3$ covalently joins an amino acid of Fc to a drug moiety. In some embodiments, $X_1$ is $(GS)_3$ (SEQ ID NO: 4) and $X_2$, $X_3$, and $X_4$ are each $(GGGGS)_4$ (SEQ ID NO: 3).

In some embodiments, the dimeric NKG2D-Fc chimera contains an IEGR (SEQ ID NO: 7) peptide linker.

Alternatively, a linking molecule may be a non-peptide linker. As used herein, a "non-peptide linker" is a biocompatible polymer including two or more repeating units linked to each other. Examples of the non-peptide polymer include but are not limited to: polyethylene glycol (PEG), polypropylene glycol (PPG), co-poly (ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacrylamide, polyacrylate, polycyanoacrylates, lipid polymers, chitins, hyaluronic acid, and heparin. For more detailed descriptions of non-peptide linkers useful for Fc fusion molecules, see, for example, WO/2006/107124, which is incorporated by reference herein. Typically such linkers will have a range of molecular weight of from about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

Drug Moieties

In some embodiments, a dimeric NKG2D-Fc chimera further comprises a drug moiety. As used herein, "drug moiety" refers to a therapeutic agent that is intended for delivery to a targeted cell (e.g., a cancer cell). Generally, a drug moiety is conjugated (e.g., directly or indirectly covalently bound) to the carboxy terminus of a dimeric NKG2D-Fc chimera. However, the skilled artisan recognizes that in some embodiments, a drug moiety is conjugated to the amino terminus of a dimeric NKG2D-Fc chimera. Examples of "drug moieties" include drugs (e.g., small molecules), toxins (e.g., molecules of the lymphotoxin family), radionuclides, enzymes, cytokines, chemokines, antibody single chain variable fragments directed against activating compounds or blocking angiogenesis, or essentially any anti-tumor compound.

In some embodiments, the drug moiety comprises a cytokine or functional portion thereof. Cytokines are proteins and peptides that are capable of modulating immune cell function. A "functional portion" of a cytokine is a cytokine fragment that retains the ability to modulate immune cell function (e.g., bind to one or more cytokine receptors). Examples of cytokines include, but are not limited to interferon-alpha (IFN-α), interferon-beta (IFN-β), and interferon-gamma (IFN-γ), interleukins (e.g., IL-1 to IL-29, in particular, IL-2, IL-5, IL-6, IL-7, IL-10, IL-12, IL-15 and IL-18), tumor necrosis factors (e.g., TNF-alpha and TNF-beta), erythropoietin (EPO), MIP3a, monocyte chemotactic protein (MCP)-1, intracellular adhesion molecule (ICAM), macrophage colony stimulating factor (M-CSF), granulocyte colony stimulating factor (G-CSF) and granulocyte-macrophage colony stimulating factor (GM-CSF). In some embodiments, the drug moiety comprises a cytokine selected from the group consisting of: IL-2, IL-12, IL-15, IL-18, IL-21 and IFN-α.

In some embodiments, a drug moiety comprises a cytokine/cytokine receptor heterocomplex. Cytokine/cytokine receptor heterocomplexes are known in the art and are described, for example in Rowley et al., Eur J Immunol. 2009 February; 39(2): 491-506. In some embodiments, a dimeric NKG2D-Fc chimera includes a drug moiety comprising an IL-15 (e.g., GenBank AAX37025)/IL-15Ra (e.g., GenBank AAP69528.1) heterocomplex. In some embodiments, the drug moiety comprises amino acids 31-107 of the human IL-15 receptor alpha (hIL15Ra, GenBank AAP69528.1) fused to amino acids 22-135 of IL-15 (GenBank AAX37025). In some embodiments, the IL-15 and IL-15Ra are separated by a linker, for example, a 20-amino acid $(G_4S)_4$ (SEQ ID NO: 3) linker. A dimeric NKG2D-Fc chimera comprising an IL-15/IL-15Ra heterocomplex is further described in the Examples section. In some embodiments, a dimeric NKG2D-Fc chimera includes a drug moiety comprising a heterocomplex of IL-12p35 and IL-12p40. In some embodiments, the IL-12p35 and IL-12p40 are separated by a linker, for example, a 20-amino acid $(G_4S)_4$ (SEQ ID NO: 3) linker. In some embodiments, a dimeric NKG2D-Fc chimera includes a drug moiety comprising a heterocomplex of IL-23p19 and IL-23p40. In some embodiments, the IL-23p19 and IL-23p40 are separated by a linker, for example, a 20-amino acid $(G_4S)_4$ (SEQ ID NO: 3) linker. In some embodiments, a dimeric NKG2D-Fc chimera includes a drug moiety comprising a heterocomplex of IL-27p28 and EB1. In some embodiments, the IL-27p28 and EB1 are separated by a linker, for example, a 20-amino acid $(G_4S)_4$ (SEQ ID NO: 3) linker. In some embodiments, each subunit of a cytokine/cytokine receptor heterocomplex is on a different chain of the dimeric NKG2D-Fc chimera.

In some embodiments, the drug moiety is an antibody single chain variable fragment (ScFv). As used herein, an "antibody single chain variable fragment" refers to a fusion protein of the variable regions of the heavy (VH) and light chains (VL) of immunoglobulins, connected with a short linker peptide. ScFv proteins retain the specificity of the original immunoglobulin, despite removal of the constant regions and the introduction of the linker. In some embodiments, a ScFv binds to an immune checkpoint protein (e.g., PD1 or CTLA4). In some embodiments, an ScFv blocks angiogenesis (e.g., binds to a regulator of angiogenesis, such as VEGF).

In some embodiments, the drug moiety is a chemokine. As used herein, "chemokines" refers to low-molecular-weight proteins that stimulate recruitment of leukocytes. Generally, chemokines are secondary pro-inflammatory mediators that are induced by primary pro-inflammatory mediators such as interleukin-1 (IL-1) or tumor necrosis factor (TNF). Chemokines can be classified into four families: CC chemokines (e.g., CCL1 to CCL-28), CXC (e.g., CXCL1 to CXCL17), C (e.g., XCL1, XCL2), and CX3C (CX3CL1).

In some embodiments, the drug moiety is a small molecule. As used herein, "small molecule" refers to a non-peptidic, non-oligomeric organic compound either synthesized in the laboratory or found in nature. Non-limiting examples of small molecule drugs include small molecule kinase inhibitors (e.g., everolimus, gefitinib, imatinib, etc.), bromodomain inhibitors (e.g., JQ1, I-BET 151, RVX-208, etc.), antibiotics (e.g., kanamycin, neomycin, ciprofloxacin, etc.), and antivirals (e.g., ribavirin, rimantadine, zidovudine, etc.). In some embodiments, the small molecule is an anti-tumor compound. Anti-tumor compounds are discussed in further detail elsewhere in this disclosure.

In some embodiments, the drug moiety is a radionuclide. As used herein, "radionuclide" refers to medically useful radionuclides. Examples of radionuclides include $^{99m}Tc$, $^{188}Re$, $^{186}Re$, $^{153}Sm$, $^{166}Ho$, $^{90}Y$, $^{89}Sr$, $^{67}Ga$, $^{68}Ga$, $^{111}In$, $^{183}Gd$, $^{225}Ac$, $^{212}Bi$, $^{211}At$, $^{45}Ti$, $^{60}Cu$, $^{61}Cu$, and $^{67}Cu$.

Other Moieties

In some embodiments, dimeric NKG2D-Fc chimeras useful for the methods described herein may further comprise one or more accessory moieties, such as a tag sequence and a signal sequence. For example, a tag sequence can be used for detecting and/or isolating the polypeptide. Examples of tags include, without limitation: HA, Flag, Myc, Glu, His and Maltose basic protein. The tag sequence may be located at the amino terminus, carboxyl terminus, or located somewhere in the middle of the dimeric NKG2D-Fc chimeric molecule (e.g., between modular peptide fragments), provided that the presence of such a tag does not interfere with the function of the dimeric NKG2D-Fc molecule. In some cases, a tag sequence is cleavable.

In some embodiments, dimeric NKG2D-Fc chimeras may optionally comprise a signal sequence. A signal sequence is a short (typically about 3-60 amino acids long) peptide chain that directs the post-translational transport of a polypeptide, thereby allowing a greater yield of the polypeptide. The amino acid sequences of a signal sequence direct polypeptides (which are synthesized in the cytosol) to certain subcellular compartments, e.g., organelles. A signal sequence is also referred to as a targeting signal, a signal peptide, a transit peptide, or a localization signal. In some embodiments, a signal sequence is cleaved from the polypeptide by signal peptidase after the polypeptide is transported.

In some embodiments, the dimeric NKG2D chimera contains an N-terminal modified IL-2 signal sequence, which allows for optimal expression and secretion of NKG2D-Fc construct. See, for example, Zhang et al., 2004, J. Gene Med., 7:354-65. In some embodiments, the dimeric NKG2D chimera contains a signal peptide derived from the polypeptide sequence of CD33. For example, the CD33 signal peptide may correspond to amino acid residues 1-16 of the CD33 polypeptide sequence. One of ordinary skill in the art will understand that there are a number of other suitable signal peptide sequences that may be used to practice the methods provided in this disclosure. In addition, where there is a signal peptide present in the NKG2D chimera, extra amino acid residues, e.g., a spacer, may be optionally inserted between the N-terminus signal peptide and the Fc portion of the chimera. In some embodiments, for example, a signal sequence is followed by a Met-Asp dipeptide spacer.

Preparation of Dimeric NKG2D-Fc

The art is familiar with molecular biological and biochemical techniques for preparing a dimeric NKG2D-Fc chimera with desired features. Preferably, dimeric NKG2D-Fc chimeric constructs are produced by conventional recombinatory DNA methods. In preferred embodiments, a dimeric NKG2D-Fc chimera is produced as a single (e.g., contiguous) recombinant polypeptide. In other embodiments, two or more portions of dimeric NKG2D-Fc are produced as separate fragments and are subsequently linked together to yield a dimeric NKG2D-Fc molecule. For example, each NKG2D portion (e.g., $NKG2D_1$, $NKG2D_2$) of the chimera and an Fc portion of the dimeric NKG2D-Fc are each produced as separate recombinant polypeptides then fused together by a chemical linking means to yield dimeric NKG2D-Fc. This production methodology may be preferred particularly in situations where a non-peptide linking molecule is employed. Similarly, this production methodology may be also preferred if a dimeric NKG2D-Fc chimera does not fold correctly (e.g., does not properly bind a ligand) when made as a single contiguous polypeptide.

For the production of recombinant polypeptides, a variety of host organisms may be used. Suitable hosts include, but are not limited to: bacteria such as *E. coli*, yeast cells, insect cells, plant cells, and mammalian cells. Choice of a suitable host organism will depend on the particular application of the dimeric NKG2D-Fc chimera. The skilled artisan will understand how to take into consideration certain criteria in selecting a suitable host for producing the recombinant polypeptide. Factors affecting selection of a suitable host include, for example, post-translational modifications, such as phosphorylation and glycosylation patterns, as well as technical factors, such as the general expected yield and the ease of purification. Host-specific post-translational modifications of a dimeric NKG2D-Fc, which is to be used in vivo, should be carefully considered because certain post-specific modifications are known to be highly immunogenic (antigenic).

Once produced, dimeric NKG2D-Fc can be purified by any suitable means, such as chromatographic methods known to those of skill in the art. Examples of chromatographic methods include gel filtration chromatography. See, for example, Caine et al., Protein Expr. Purif., 1996, 8:159-66. In some embodiments, dimeric NKG2D-Fc is purified by Protein A immunoaffinity chromatography.

As will be recognized by one of ordinary skill in the art, dimeric NKG2D chimera portions also can be prepared and isolated separately, and joined by chemical synthesis.

NKG2D Receptor Ligands

In any of the embodiments described in this disclosure, dimeric NKG2D-Fc is capable of binding the endogenous ligand of the NKG2D receptor. Known NKG2D-ligands in humans include MICA, MICB, RAET-1G, ULBP1, ULBP2, ULBP3, ULBP4, ULBP5, and ULBP6. Preferably, the dimeric NKG2D-Fc chimera descried in the present disclosure is capable of binding more than one type of NKG2D receptor ligand.

In some embodiments, the dimeric NKG2D-Fc chimeric molecules bind ligands with high affinity of $10^{-4}$ M or less, $10^{-7}$ M or less, or with subnanomolar affinity, e.g., 0.9, 0.8, 0.7, 0.6, 0.5, 0.4, 0.3, 0.2, 0.1 nM or even less. In some embodiments, the binding affinity of the dimeric NKG2D-Fc molecule for its ligands is at least $5\times10^6$ Ka, at least $1\times10^7$ Ka, at least $2\times10^7$ Ka, at least $1\times10^8$ Ka, or greater.

In some embodiments, NKG2D-Fc binds preferentially to (e.g., with higher affinity for) a subset of NKG2D receptor ligands. 3D structural data in combination with mutagenesis analyses have revealed that NKG2D is permissive in the recognition and binding of a diverse array of its endogenous ligands.

A ligand for NKG2D may be expressed on a cell surface. Alternatively, a ligand for NKG2D may be "shed" from the cell surface and is present as a soluble ligand. It has been known in certain cancers that NKG2D ligands such as MICA are over-expressed and in some cases released (e.g., shed) into the bloodstream or surrounding tissues in a soluble form, e.g., in sera. It is believed that this contributes, at least in part, to the pathogenesis and/or progression of cancer. Thus, the dimeric NKG2D-Fc is useful for binding such ligand, either present on cell surface or as a released form, in counterbalancing the expression of the ligands that are present at an abnormally elevated level by functioning as a neutralizing agent.

Where an NKG2D ligand is expressed on the surface of cancer cells of a subject, dimeric NKG2D-Fc described in the present disclosure binds to the cell surface ligand when administered to the subject. The binding of the dimeric NKG2D-Fc chimera to its ligand may prevent activation of endogenous NKG2D receptors present on NK cells. Where an NKG2D ligand is "shed" from cancer cells, e.g., released into the bloodstream of a subject, dimeric NKG2D-Fc described herein binds to the soluble ligand, sequestering it from further action.

Therapeutic Applications

Normally, expression of the NKG2D ligands appears to be confined to the gastrointestinal epithelium. Little expression is observed in quiescent epithelial cells, but higher levels of expression occur in rapidly proliferating cells. Expression of the NKG2D ligands is also up-regulated in various transformed cells, particularly those of epithelial origin. Accordingly, provided herein are methods for treating cancer or symptoms of cancer in a subject. The methods comprise administering to the subject a therapeutically effective amount of dimeric NKG2D-Fc that binds NKG2D ligands in vivo.

The terms "treating," "treatment," and "treat" and the like in the context of a cancer therapy refer to the administration of a composition comprising dimeric NKG2D-Fc as described herein to a subject who has cancer. The composition is administered to the subject in an amount that is therapeutically effective. As used herein, a therapeutically effective amount refers to an amount of the therapeutic that is believed to effectuate a beneficial effect with statistical significance on the subject having the disease or disorder, such as certain types of cancer. Generally, a therapeutically effective amount is determined by administering the composition to a population of subjects with specified conditions (such as progression or stage of a disease) and evaluating the outcome in response. As used herein, therapeutic treatment shall include, for example, complete prevention or abolishment of the symptoms of a disease, a delay in onset of the symptoms of a disease, or lessening in the severity of a disease.

Cancer

Dimeric NKG2D-Fc chimeras are believed to be broadly useful for immunotherapy for a wide variety of cancers, where the expression of one or more NKG2D ligands is elevated in a subject. Cancer broadly refers to a proliferative disease involving transformed cells, including both pre-malignant and malignant disorders. The present invention is useful for treating a subject having cancer that is characterized by over-expression of one or more NKG2D ligands. In some embodiments, the cancer is characterized by over-expression of one (or predominantly one) ligand of the NKG2D receptor. In other embodiments, the cancer is characterized by over-expression of two or more NKG2D ligands.

The methods disclosed herein are useful therapeutics for the treatment of pre-malignant disorders that carry with them a risk of progressing to malignancy.

Examples of such disorders include, without limitation, dysplasia, hyperplasia, and plasma cell disorders such as monoclonal gammopathy of undetermined significance (MGUS) and smoldering multiple myeloma (SMM). In some embodiments, the cancer is melanoma, lung, breast, kidney, ovarian, prostate, pancreatic, gastric, and colon carcinoma, lymphoma or leukemia. In some embodiments, the cancer is melanoma. In some embodiments, the cancer is a plasma cell malignancy, for example, multiple myeloma (MM) or pre-malignant condition of plasma cells. In some embodiments, the cancer is melanoma, lung cancer, plasma cell cancer, leukemia, lymphoma, ovarian cancer, colon cancer, pancreatic cancer or prostate cancer. In some embodiments, the subject has been diagnosed as having a cancer or as being predisposed to cancer. Thus, methods disclosed herein are also useful to treat a subject who has had a metastasis and is therefore susceptible to a relapse or recurrence. The methods are particularly useful in high-risk individuals who, for example, have a family history of cancer or metastasizing tumors, or show a genetic predispositions for a cancer metastasis. Specifically, the methods are directed to treating cancer that is associated with NKG2D ligand expression. In some embodiments, an NKG2D ligand is MICA. Thus, in some embodiments, the cancer causes MICA-related tumors.

Whether a particular subject (e.g., patient) should receive a cancer therapy comprising NKG2D-Fc can be determined by testing for aberrant expression of one or more NKG2D ligands in the subject. "Aberrant expression of one or more NKG2D ligands" in the subject means over-expression of the ligand(s) in a biological sample obtained from the subject. In some embodiments, a biological sample may include a biopsy sample taken from a tissue of the subject suspected to be cancerous. For example, in some cases, a biological sample is collected from a solid tumor to test for malignancy. In other cases, a biological sample may constitute a blood sample, e.g., serum, a stool sample, urine sample, etc. A biological sample may be any cell or tissue sample that is collected from a subject for the purpose of testing for the diagnosis or progression of a disease, such as cancer.

One of ordinary skill in the art is familiar with a variety of laboratory techniques and protocols used to assay for the presence of and the levels of one or more markers present in a biological sample. To determine whether a subject has cancer that is associated with over-expression of NKG2D ligand(s), typically immunoaffinity assays are performed. In certain situations, depending on the type of biological samples that are available, immunohistological or immunocytochemical analyses may be carried out. A number of antibodies are commercially available for performing these analyses. Methods commonly employed for this purpose include, but are not limited to, ELISA, immunoblotting, and immunohistochemistry.

Subjects

The methods disclosed herein can be applied to a wide range of species, e.g., humans, non-human primates (e.g., monkeys), horses, cattle, pigs, sheep, deer, elk, goats, dogs, cats, rabbits, guinea pigs, hamsters, rats, and mice, which are known to develop cancer. Thus, a "subject" as used herein is a mammalian subject having a disease, or at risk of developing a disease associated with an abnormal expression of at least one NKG2D ligand, such as cancer. In preferred embodiments, the subject is a human subject having a cancer presenting elevated levels of one or more NKG2D ligands. In some embodiments, the NKG2D ligands include MICA.

If a subject has been shown to express an elevated level of one or more NKG2D ligands, the subject may be treated with the methods described herein. In some circumstances, a subject has received or is receiving another cancer therapy. In some embodiments, the cancer may be in remission. In some cases, the subject is at risk of having recurrence, e.g., metastasis. In some embodiments, the over-expression of one or more NKG2D ligands is limited to cancerous cells, e.g., tumors. In some embodiments, at least one of the NKG2D ligands expressed by cancer cells are shed into the blood stream, and thus detectable in the serum of the subject. Depending on the phenotype of a particular cancer, it may be possible to target one or more ligands which are over-expressed (expressed by tumor cells) over the other ligands, whose expression is not significantly affected.

Modes of Action

The instant invention is based, in part, on the surprising discovery that that a chimeric molecule comprising two NKG2D fragments and an Fc fragment (e.g., a dimeric NKG2D-Fc chimera), which is capable of binding one or more NKG2D ligands, induces tumor cell death with improved efficacy compared to chimeric molecules comprising a single NKG2D fragment and an Fc fragment (e.g., a monomeric NKG2D-Fc chimera).

Without being limited by any particular theory, it appears that dimeric NKG2D-Fc chimeras can function through the two major components of the immune system: innate immunity and adaptive immunity. As used herein, innate immunity or the innate immune system refers to non-specific host defense mechanisms against foreign pathogens. Innate immunity includes both physical barriers (e.g., skin, gastric acid, mucus or tears, as well as cells) and active mechanisms such as NK cells, phagocytes and the complement system. NK cells represent a major component of the innate immune system. NK cells are cytotoxic, e.g., are able to attack cells that have been infected by microbes, as well as some kinds of tumor cells. The cytotoxic activity of NK cells is mediated through cell-surface receptors that recognize MHC class I alleles. A number of receptor types are known in the art, including NKG2D, which is one receptor subtype. Phagocytic cells include neutrophils, monocytes, macrophages, basophils and eosinophils. The complement system is a biochemical cascade of the immune system that helps clear pathogens from a host organism.

In general, adaptive immunity or the adaptive immune system refers to an antigen-specific antibody-mediated immune response. Adaptive immunity is generally mediated via specific antibody production by B lymphocytes and antigen-specific activity of T lymphocytes. The humoral response mediated by B lymphocytes defends primarily against extracellular pathogens through the production of circulating antibodies that mark foreign cells and molecules for destruction by other specialized cells and proteins. The cellular response mediated by T lymphocytes defends predominantly against intracellular pathogens and cancer cells by directly binding to and destroying the affected cells. According to the present disclosure, dimeric NKG2D-Fc, which is a non-antibody molecule, is believed to functionally mimic what is ordinarily the function of specific antibodies.

The present invention thus contemplates methods for cancer treatment, wherein dimeric NKG2D-Fc binds directly to tumor cells that are expressing NKG2D ligands on the cell surface. In this mode of action, dimeric NKG2D-Fc can specifically identify for destruction tumor cells that over-express NKG2D ligands, but not healthy cells that do not.

Dimeric NKG2D-Fc can target any or all NKG2D ligands that are expressed on human tumor cells in at least two ways. One mechanism of mediating tumor cell destruction is through the process of complement lysis (also referred to as complement dependent lysis, complement-dependent cytotoxicity or CDC). A second way of mediating tumor cell destruction is by triggering antibody dependent cellular cytotoxicity (ADCC).

In some embodiments, dimeric NKG2D-Fc acts as an opsonizing agent. Opsonization is the process where cells or particles become coated with molecules which allow them to bind to receptors on other cells, such as dendritic cells or phagocytes, to promote the uptake. For antigen-presenting cells such as dendritic cells and macrophages, opsonization promotes efficient processing and presentation of antigens. Opsonizing agents that are capable of specifically binding to both the target (e.g., ligands) and particular receptors on antigen-presenting cells (e.g., FcRs) that can mediate internalization and subsequent antigen processing are particularly useful.

Tumor cells that express one or more ligands of the NKG2D receptor on the cell surface can become opsonized, e.g., coated, with dimeric NKG2D-Fc molecules. For example, the NKG2D portion of the chimera can bind to the ligands on the tumor cell surface, while leaving the Fc portion of the chimera exposed. Dendritic cells have FcγRs and therefore can bind to and internalize the tumor antigen (e.g., NKG2D ligands), which then results in antigen presentation to cytotoxic T cells, also known as CD8+ T cells. This is referred to as cross-priming. Similarly, opsonization results in the generation of MHC class II-restricted CD4+ T cell responses. Through opsonization, therefore, the NKG2D-Fc chimera can promote efficient cross-presentation (e.g., priming) by dendritic cells, leading to the induction of potent T cell responses against the tumor.

Cancer patients often suffer from immune suppression. In some cases, it is believed that the immune suppression, at least in part, may be caused by impaired NKG2D receptor signaling. Based on a prevailing model, for example, shed MICA impairs host defense by inducing the internalization of NKG2D receptor molecules on lymphocytes. Thus, according to this model, tumor cell shedding of MICA results in immune suppression through down-regulation of NKG2D surface expression.

Therefore, the methods provided herein are useful for counteracting or relieving immune suppression by administering a composition comprising dimeric NKG2D-Fc, particularly in situations where a patient exhibits elevated levels of soluble (i.e., shed) NKG2D ligand or ligands that are detectable in sera. The mode of action is that NKG2D-Fc administered to the patient binds to (thus sequestering)

excess soluble ligands of NKG2D that were shed from tumors, thereby reversing the down-expression of NKG2D receptors on cell surface that led to immune suppression.

Thus, the dimeric NKG2D-Fc chimera can have multiple therapeutic functions, including neutralizing soluble ligands that are shed by tumor cells, promoting ADCC and/or CDC in tumor cells expressing the cell surface ligands and mediating cross presentation and priming of the adaptive immune system, including CD8 cytotoxic T-lymphocytes (CTLs) and tumor-specific antibody producing B-cells.

Administration

The dimeric NKG2D-Fc composition can be administered directly to a subject. The subject is preferably a mammal. The terms "administration" and "administer" refer to a means of providing a pharmaceutical agent to a subject such that the pharmaceutical agent is to contact its target cells, e.g., cancer cells, in vivo, i.e., in the body of the subject. In some embodiments, the composition comprising NKG2D-Fc is systematically administered to a subject. In preferred embodiments, a systematic administration is delivered via an intravenous injection. In some embodiments, the composition comprising dimeric NKG2D-Fc is administered locally. For example, in some cases, the composition may be delivered directly to or within close proximity of a solid tumor.

Pharmaceutically-Acceptable Carriers

In some aspects, the disclosure provides a composition comprising the dimeric NKG2D-Fc chimera as described by this document and a pharmaceutically acceptable carrier. Generally, the composition comprising dimeric NKG2D-Fc can be suspended in a pharmaceutically-acceptable carrier (e.g., physiological saline). Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters, for example. Aqueous earners include, without limitation, water, alcohol, saline, and buffered solutions. Preservatives, flavorings, and other additives such as, for example, antimicrobials, anti-oxidants, chelating agents, inert gases, and the like also may be present. It will be appreciated that any material described herein that is to be administered to a mammal can contain one or more pharmaceutically acceptable carriers.

Routes of Administration

Any composition described herein can be administered to any part of the subject's body via various administration routes. The composition can be administered by intravenous, intraperitoneal, intramuscular, subcutaneous, intramuscular, intrarectal, intravaginal, intrathecal, intratracheal, intradermal, or transdermal injection, by oral or nasal administration, by inhalation, or by gradual perfusion over time. The composition can be delivered to specific tissue. For example, the composition can be delivered to, without limitation, the joints, nasal mucosa, blood, lungs, intestines, muscle tissues, skin, or peritoneal cavity of a mammal. In a further example, an aerosol preparation of a composition can be given to a subject by inhalation.

Dosage

The dosage required depends on the route of administration, the nature of the formulation, the nature of the patient's illness, the subject's size, weight, surface area, age, and sex, other drugs being administered, and the judgment of the attending physician. Suitable dosages are typically in the range of 0.01-1,000 µg/kg. Wide variations in the needed dosage are to be expected in view of the variety of dimeric NKG2D-Fc compositions available and the differing efficiencies of various routes of administration. Variations in these dosage levels can be adjusted using standard empirical routines for optimization as is well understood in the art. Administrations can be single or multiple (e.g., 2- or 3-, 4-, 6-, 8-, 10-, 20-, 50-, 100, 150-, or more fold). Encapsulation of the composition in a suitable delivery vehicle (e.g., polymeric microparticles or implantable devices) may increase the efficiency of delivery.

Treatment Regimen

The duration of treatment with any composition provided herein can be any length of time from as short as one day to as long as the life span of the host (e.g., many years). For example, dimeric NKG2D-Fc compositions can be administered once a month for three months, or once a year for a period of ten years. It is also noted that the frequency of treatment can be variable. For example, dimeric NKG2D-Fc compositions can be administered once (or twice, three times, etc.) daily, weekly, monthly, or yearly. Dimeric NKG2D-Fc compositions can be administered together, e.g., at the same point in time or sequentially, with one or more other cancer therapies. For example, a patient can receive an autologous tumor cell vaccine followed by an anti-CTL4 antibody, followed by a dimeric NKG2D-Fc therapy, separated by intervals of hours, days, months or years.

Effective Amounts

An effective amount of any composition described herein can be administered to a subject. The term "effective" as used herein refers to any amount that induces a desired therapeutic effect, such as an immune response, while not inducing significant toxicity in the subject. Such an amount can be determined by assessing a subject's biological reaction, e.g., immune response and improvement in a symptom, after administration of a known amount of a particular composition. In addition, the level of toxicity, if any, can be determined by assessing a subject's clinical symptoms before and after administering a known amount of a particular composition. It is noted that the effective amount of a particular composition administered to a subject can be adjusted according to a desired outcome as well as the host's response and level of toxicity. Significant toxicity can vary for each particular host and depends on multiple factors including, without limitation, the subject's disease state, age, and tolerance to pain.

Combination Therapy

In some embodiments, the subject in need of cancer treatment is treated with the dimeric NKG2D-Fc composition described herein in conjunction with additional cancer therapy. In some embodiments, the additional cancer therapy includes a cytotoxic agent and/or non-cytotoxic agent. A "cytotoxic agent" refers to a substance that inhibits or prevents the function of cells and/or causes destruction of cells. The term is intended to include radioactive isotopes (e.g., $^{131}$I, $^{125}$I, $^{90}$Y and $^{186}$Re), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A "non-cytotoxic agent" may include an agent that can be activated to be cytotoxic. A non-cytotoxic agent may include a bead, liposome, matrix or particle (see, e.g., U. S. Patent Publications 2003/0028071 and 2003/0032995, which are incorporated by reference herein). Such agents may be conjugated, coupled, linked or associated with a dimeric NKG2D-Fc composition described herein.

In some embodiments, conventional cancer medicaments are administered with the compositions described herein. In some cases, the subject in need of cancer treatment is treated with the dimeric NKG2D-Fc composition described herein in conjunction with one or more additional agents directed to target cancer cells. Highly suitable agents include those agents that promote DNA-damage, e.g., double stranded breaks in cellular DNA, in cancer cells. Any form of DNA-damaging agent know to those of skill in the art can be used. DNA damage can typically be produced by radiation therapy and/or chemotherapy. DNA-damaging agents are also referred to as genotoxic agents. As used herein, "in conjunction with" shall mean that dimeric NKG2D-Fc is administered to a subject concurrently with one or more additional therapies (either simultaneously or separately but in close proximity), prior to, or after administration of one or more additional therapies.

Examples of radiation therapy include, without limitation, external radiation therapy and internal radiation therapy (also called brachytherapy) Energy sources for external radiation therapy include x-rays, gamma rays and particle beams, energy sources used in internal radiation include radioactive iodine (iodine$^{125}$ or iodine$^{131}$), strontium$^{89}$, or radioisotopes of phosphorous, palladium, cesium, indium, phosphate, or cobalt. Methods of administering radiation therapy are well known to those of skill in the art.

Examples of DNA-damaging chemotherapeutic agents that may be particularly useful include, without limitation: Busulfan (Myleran), Carboplatin (Paraplatin), Carmustme (BCNU), Chlorambucil (Leukeran), Cisplatin (Platmol), Cyclophosphamide (Cytoxan, Neosar), Dacarbazme (DTIC-Dome), Ifosfamide (Ifex), Lomustme (CCNU), Mechlorethamme (nitrogen mustard, Mustargen), Melphalan (Alkeran), and Procarbazine (Matulane).

A number of other chemotherapeutic agents may be also used for the method described herein, either alone or in combination. These include: methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, cisplatin, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analog), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26), and Vindesine sulfate, but it is not so limited.

In addition, the following agents may be also useful for the instant invention: alkylating agents, such as carboplatin and cisplatin, nitrogen mustard alkylating agents, nitrosourea alkylating agents, such as carmustine (BCNU), antimetabolites, such as methotrexate, folinic acid, purine analog antimetabolites, mercaptopurine, pyrimidine analog antimetabolites, such as fluorouracil (5-FU) and gemcitabine (Gemzar®), hormonal antineoplastics, such as goserelin, leuprolide, and tamoxifen, natural antineoplastics, such as aldesleukin, interleukin-2, docetaxel, etoposide (VP-16), interferon alfa, paclitaxel (Taxol®), and tretinoin (ATRA), antibiotic natural antineoplastics, such as bleomycin, dactmomycin, daunorubicin, doxorubicin, daunomycin and mitomycins including mitomycin C, and vinca alkaloid natural antineoplastics, such as vinblastine, vincristine, vindesine, hydroxyurea, acetone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxan®), Schizophyllan, cytarabine (cytosine arabinoside), dacarbazine, thiomosine, thiotepa, tegafur, dolastatins, dolastatin analogs such as auristatin, CPT-11 (irinotecan), mitozantrone, vinorelbine, teniposide, aminopterin, carbomycin, esperamicins (See, e.g., U.S. Pat. No. 4,675,187, which is incorporated by reference herein), neocarzinostatin, OK 432, bleomycin, furtulon, broxundine, busulfan, honvan, peplomycin, bestatin (Ubenimex®), interferon-β, mepitiostane, mitobromtol, melphalan, laminin peptides, lentinan, *Coriolus versicolor* extract, tegafur/uracil, estramustine (estrogen/mechlorethamine), thalidomide, and lenalidomide (Revlmid®).

Other suitable chemotherapeutics include proteasome inhibiting agents. Proteasome inhibitors block the action of proteasomes, cellular complexes that degrade proteins, particularly those short-lived proteins that are involved in cell maintenance, growth, division, and cell death. Examples of proteasome inhibitors include bortezomib (Velcade®), lactacystin (AG Scientific, Inc, San Diego, CA), MG132 (Biomol International, Plymouth Meeting, PA) PS-519, eponemycin, epoxomycin, aclacinomycin A, the dipeptide benzamide, CVT-63417, and vinyl sulfone tripeptide proteasome inhibitors.

In some embodiments, the methods described herein are used in conjunction with one or more other cancer treatments, including cancer immunotherapy. Cancer immunotherapy is the use of the immune system to reject cancer. The main premise is stimulating the subject's immune system to attack the tumor cells that are responsible for the disease. This can be either through immunization of the subject, in which case the subject's own immune system is rendered to recognize tumor cells as targets to be destroyed, or through the administration of therapeutics, such as antibodies, as drugs, in which case the subject's immune system is recruited to destroy tumor cells by the therapeutic agents. Cancer immunotherapy includes an antibody-based therapy and cytokine-based therapy.

A number of therapeutic monoclonal antibodies have been approved by the FDA for use in humans, and more are underway. The FDA-approved monoclonal antibodies for cancer immunotherapy include antibodies against CD52, CD33, CD20, ErbB2, vascular endothelial growth factor and epidermal growth factor receptor. These and other antibodies targeting one or more cancer-associated antigen are thus suitable for use in a combination therapy to be administered in conjunction with dimeric NKG2D-Fc. Examples of monoclonal antibodies approved by the FDA for cancer therapy include, without limitation: Rituximab (available as Rituxan™), Trastuzumab (available as Herceptin™), Alemtuzumab (available as Campath-IH™), Cetuximab (available as Erbitux™), Bevacizumab (available as Avastin™) Panitumumab (available as Vectibix™), Gemtuzumab ozogamicin (available as Mylotarg™) Ibritumomab tiuxetan (available as Zevalin™) and Tositumomab (available as Bexxar™) Examples of monoclonal antibodies currently undergoing human clinical testing for cancer therapy in the United States include, without limitation: WX-G250 (available as Rencarex™) Ipilimumab (available as MDX-010), Zanolimumab (available as HuMax-CD4), Ofatunumab (available as HuMax-CD20), ch14.18, Zalutumumab (available as HuMax-EGFr), Oregovomab (available as B43.13, OvalRex™), Edrecolomab (available as IGN-101, Panorex™), 131I-chTNT-I/B (available as Cotara™), Pemtumomab (available as R-1549, Theragyn™), Lintuzumab (available as SGN-33), Labetuzumab (available as hMN14, CEAcide™) Catumaxomab (available as Removab™), CNTO 328 (available as cCLB8), 3F8, 177Lu-J591, Nimotuzumab, SGN-30, Ticilimumab (available as CP-675206), Daclizumab (available as Zenapax™), Epratuzumab (available as hLL2, LymphoCide™), $^{90}$Y-Epratuzumab, Galiximab (available as IDEC-114), MDX-060, CT-011, CS-1008, SGN-40, Mapatumumab (available as TRM-I), Apolizumab (available as HuID10, Remitogen™) and Volociximab (available as M200).

Cancer immunotherapy also includes a cytokine-based therapy. The cytokine-based cancer therapy utilizes one or more cytokines that modulate a subject's immune response. Non-limiting examples of cytokines useful in cancer treatment include interferon-α (IFN-α), interleukin-2 (IL-2), Granulocyte-macrophage colony-stimulating factor (GM-CSF) and interleukin-12 (IL-12).

The entire contents of all of the references (including literature references, issued patents, published patent applications, and co pending patent applications) cited throughout this application are hereby expressly incorporated by reference.

EXAMPLES

Constructs
hIgG1
This construct is the hIgG1 portion from the parental pFUSE-hIgG1 vector (Invivogen).
hNKG2Dx2-hIgG1
Two copies of human NKG2D (F78-V216), with an amino acid spacer between them, were cloned via restriction-free cloning 5' of the pFUSE-hIgG1 vector (Invivogen). A schematic of this construct is depicted in FIG. 1, left panel.

```
hNKG2D, RefSeq NP_031386.2 , amino acids
78-216:
                                    (SEQ ID NO: 1)
FLNSLFNQEVQIPLTESYCGPCPKNWICYKNNCYQFFDESKNW

YESQASCMSQNASLLKVYSKEDQDLLKLVKSYHWMGLVHIPTN

GSWQWEDGSILSPNLLTIIEMQKGDCALYASSFKGYIENCSTP

NTYICMQRTV
``` hIgG1-X or hNKG2Dx2-hIgG1-X
Using either the hIgG1 vector or the hNKG2Dx2-hIgG1 parental vectors, described above, various constructs were cloned 3' of the hIgG1 segment (denoted by "X" above). These constructs are described below.
hIL15/hIL15Ra
A codon optimized version of a portion of the human IL-15 receptor alpha (hIL15Ra, GenBank AAP69528.1, amino acids 31-107, was fused to a codon optimized version of IL-15 (IL15, GenBank AAX37025, amino acids 22-135. The hIL15Ra and hIL-15 were separated by a twenty amino acid (G$_4$S)$_4$ (SEQ ID NO: 3) linker. Amino acid sequences are shown below.

```
hIL15Ra, GenBank AAP69528.1, amino acids
31-107:
                                    (SEQ ID NO: 8)
ITCPPPMSVEHADIWVKSYSLYSRERYICNSGFKRKAGTSSLT

ECVLNKATNVAHWTTPSLKCIRDPALVHQRPAPP

IL15, GenBank AAX37025, amino acids 22-135:
                                    (SEQ ID NO: 9)
NWVNVISDLKKIEDLIQSMHIDATLYTESDVHPSCKVTAMKCF

LLELQVISLESGDASIHDTVENLIILANNSLSSNGNVTESGCK

Figure 3:
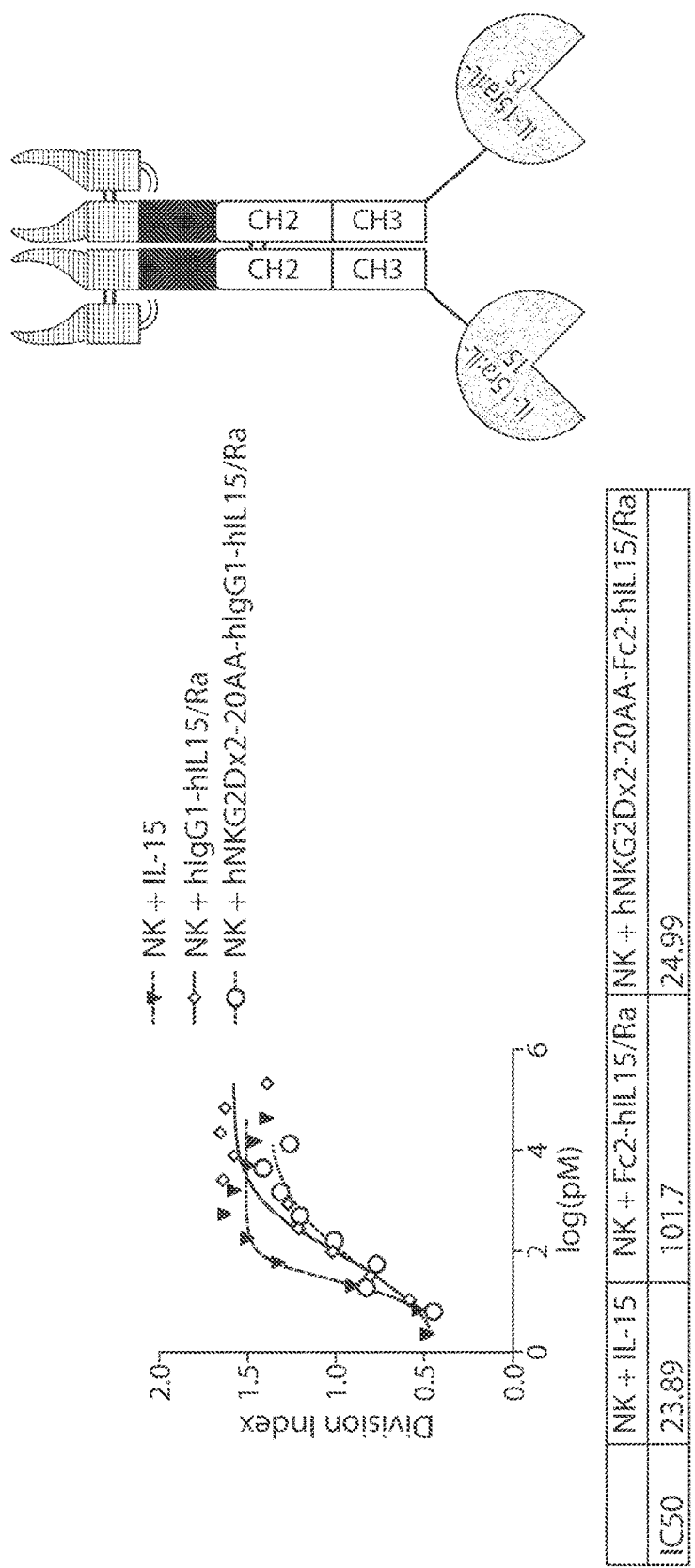
FIG. 3 shows that hNKG2Dx2-hIgG1-IL15/Ra promotes proliferation of human NK cells similarly to IL-15.

ECEELEEKNIKEFLQSFVHIVQMFINTS
``` aPD1
The ScFv for anti-mouse PD1 was cloned 3' of the hIgG1 segment in the hIgG1 vector or the hNKG2Dx2-hIgG1 vector.
aCTLA4
The ScFv for anti-mouse CTLA4 was cloned 3' of the hIgG1 segment in the hIgG1 vector or the hNKG2Dx2-hIgG1 vector.
Heterologous Expression and Purification
The indicated fusion constructs were produced in 293FT cells by calcium phosphate transfection of plasmids encoding the constructs. Supernatants were collected, and the fusion constructs were purified by Protein A chromatography. 1 µg of each construct (reduced with 2-mercaptoethanol and heated to 70° C. for 10 minutes or not) was loaded onto an 8-10% SDS-PAGE gel, run at 100V for 60-120 minutes, and proteins were visualized with Coomassie Blue staining. FIG. 2 shows that hNKG2Dx2-hIgG1-hIL15/Ra is produced as a single fusion protein, and is easily purified by protein A.
Proliferation Assay
Human NK cells were isolated from normal donors using RosetteSep (StemCell Technologies). NK cells were labeled with 5 µM carboxyfluorescein succinimidyl ester (CFSE) (Invitrogen). Cells were then cultured in RPMI+10% FBS with various dilutions of the IL-15 constructs (hIgG1-hIL15/Ra or hNKG2Dx2-20AA-hIgG1-hIL15/Ra) or IL-15 for 4 days, and CFSE dilution was measured using a FACSCanto (BD). FIG. 3 provides results showing that incubation with hNKG2Dx2-hIgG1-IL15/Ra promotes proliferation of human NK cells similarly to incubation with IL-15.

Killing Assay

Human NK cells were isolated from normal donors using RosetteSep (StemCell Technologies), and frozen in BamBanker (Wako). NK cells were thawed, and allowed to recover overnight in RPMI+10% FBS+200 IU/mL hIL-2. Cells were then washed three times in PBS, and added to various tumor targets previously labeled with CFSE (Invitrogen). Cells were centrifuged for 1 minute at 1000 rpm, and co-cultured for 5 hours at 37 degrees in a humidified CO2 incubator. After 4 hours, 7-aminoactinomycin D (7-AAD) was added, and tumor target cell death was analyzed.

Figure 4:
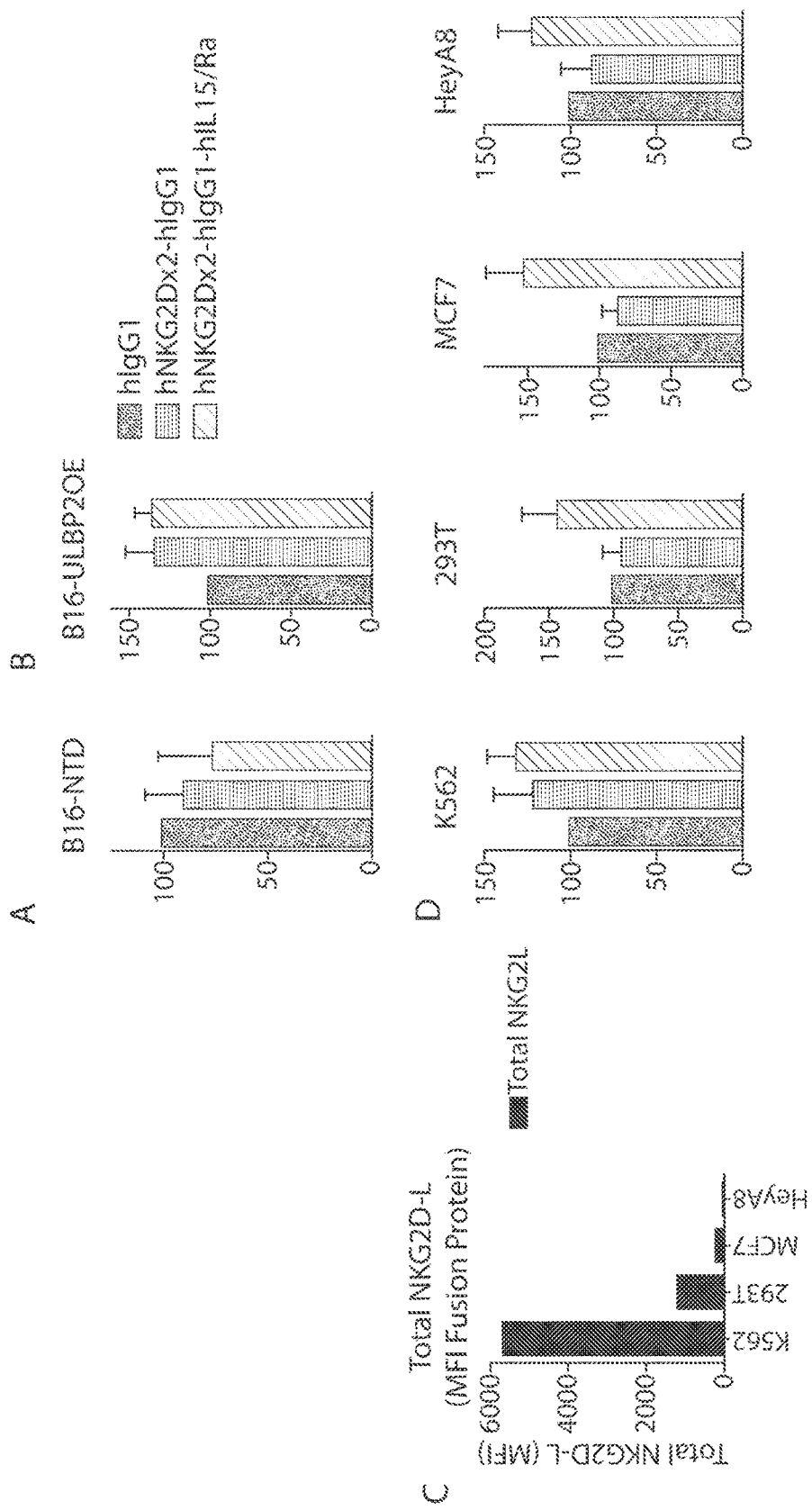
FIG. 4 shows that hNKG2Dx2-hIgG1-IL15/Ra promotes potent killing of multiple cell lines, and is superior to hNKG2Dx2-hIgG1 in cell lines with moderate ligand expression. Panel A shows that neither construct promotes killing of the B16 tumor cell line, which does not express NG2D-L. Panel B shows that both constructs equally promote killing of a synthetic B16 tumor cell line expressing high levels of NKG2D ligand. Panel C shows that various tumors express different levels of NKG2D ligands on their cell surface, as measured by NKG2D fusion protein binding. Panel D shows that hNKG2Dx2-hIgG1-IL15/Ra kills cells expressing moderate NKG2D ligand more efficiently than hNKG2Dx2-hIgG1.

FIG. 4 shows that hNKG2Dx2-hIgG1-IL15/Ra promotes potent killing of multiple cell lines, and is superior to hNKG2Dx2-hIgG1 in cell lines with moderate ligand expression. Panel A shows that constructs do not promote killing of the B16 tumor cell line, which does not express NG2D-L. Both hNKG2Dx2-hIgG1 and hNKG2Dx2-hIgG1-IL15/Ra constructs equally promote killing of a synthetic B16 tumor cell line expressing high levels of NKG2D ligand (FIG. 4, panel B). Various tumors express different levels of NKG2D ligands on their cell surface, as measured by NKG2D fusion protein binding (FIG. 4, panel C). The hNKG2Dx2-hIgG1 and hNKG2Dx2-hIgG1-IL15/Ra constructs also promote killing of tumors naturally expressing high levels of NKG2D ligands (K562), but the hNKG2Dx2-hIgG1-IL15/Ra construct drives superior killing, in a graded manner inversely correlated with NKG2D ligand expression (FIG. 4, panel D).

IFNγ ELISA

Human NK cells were isolated, frozen, and added to tumor targets as described above, except that there was no overnight recovery period for the NK cells (e.g., RPMI+10% FBS+200 IU/mL hIL-2), and tumor targets were not labeled with CFSE. After 24 hours of co-culture, the plates were spun down and supernatant was aspirated for analysis by IFN-γ ELISA (Becton Dickinson).

Figure 5:
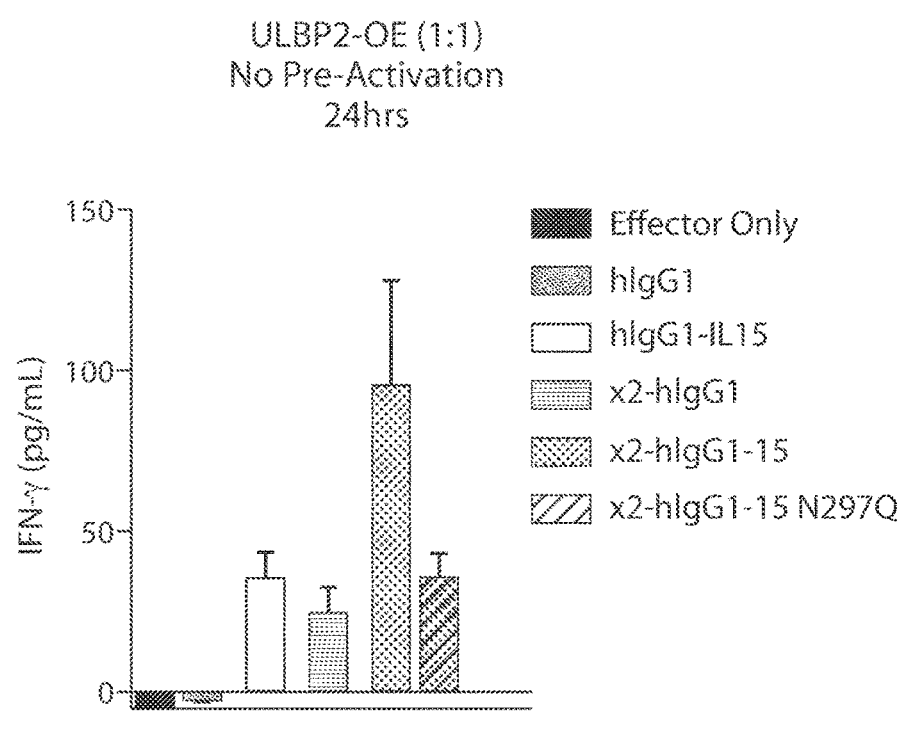
FIG. 5 shows that resting NK cells are activated by the fusion protein to produce IFN-γ, but maximum production requires all three components: NKG2D, hIgG1, and IL-15. N297Q is a mutation in hIgG1 that prevents CD16 (expressed on NK) binding to hIgG1.

FIG. 5 shows that resting NK cells are activated by the fusion protein to produce IFN-γ, but maximum production requires all three components: NKG2D, hIgG1, and IL-15. Note that N297Q is a mutation in hIgG1 that prevents CD16 (expressed on NK) binding to hIgG1.

CD16 and IL-15 Activation

Figure 6:
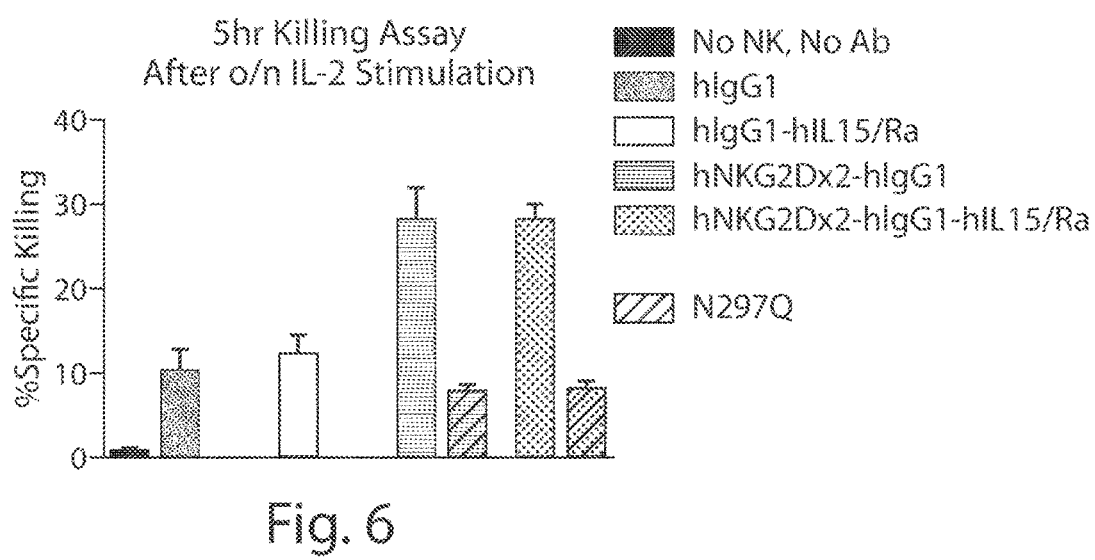
FIG. 6 shows that pre-activated NK cells require CD16 binding to kill target cells, but do not require IL-15.

FIG. 6 shows that pre-activated NK cells (e.g., incubated overnight with hIL-2) require CD16 binding to kill target cells, but do not require IL-15.

Figure 7:
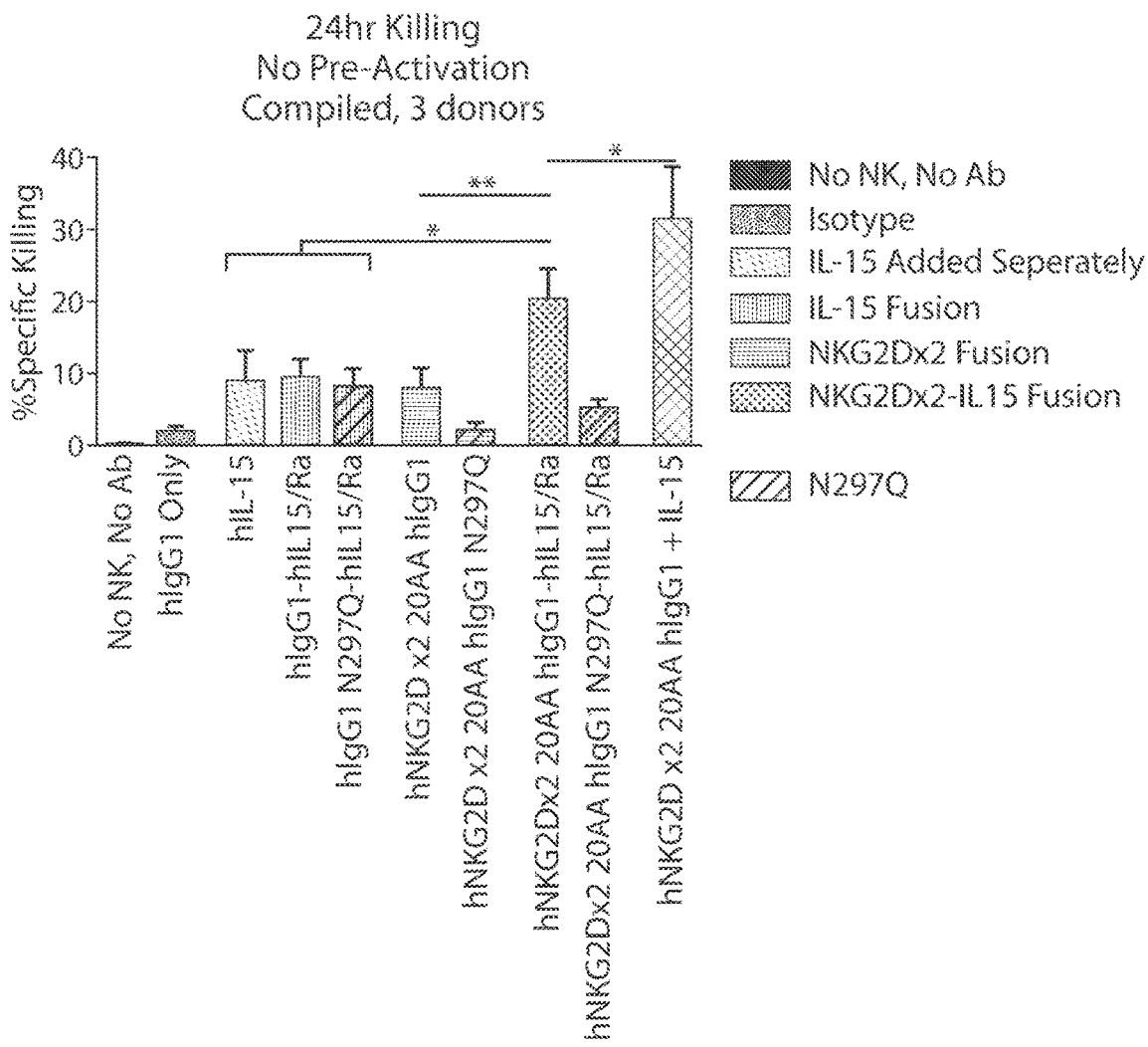
FIG. 7 shows that optimal activation of, and killing by, resting NK cells requires CD16 binding and IL-15 activation.

Human NK cells were isolated, frozen, and added to tumor targets, as described above. There was no overnight recovery period for the NK cells. Tumor targets were labeled with CFSE. FIG. 7 shows that optimal activation of, and killing by, resting NK cells requires CD16 binding and IL-15 activation.

Improved Characteristics of Dimeric NKG2D-Fc Constructs

Figure 8:
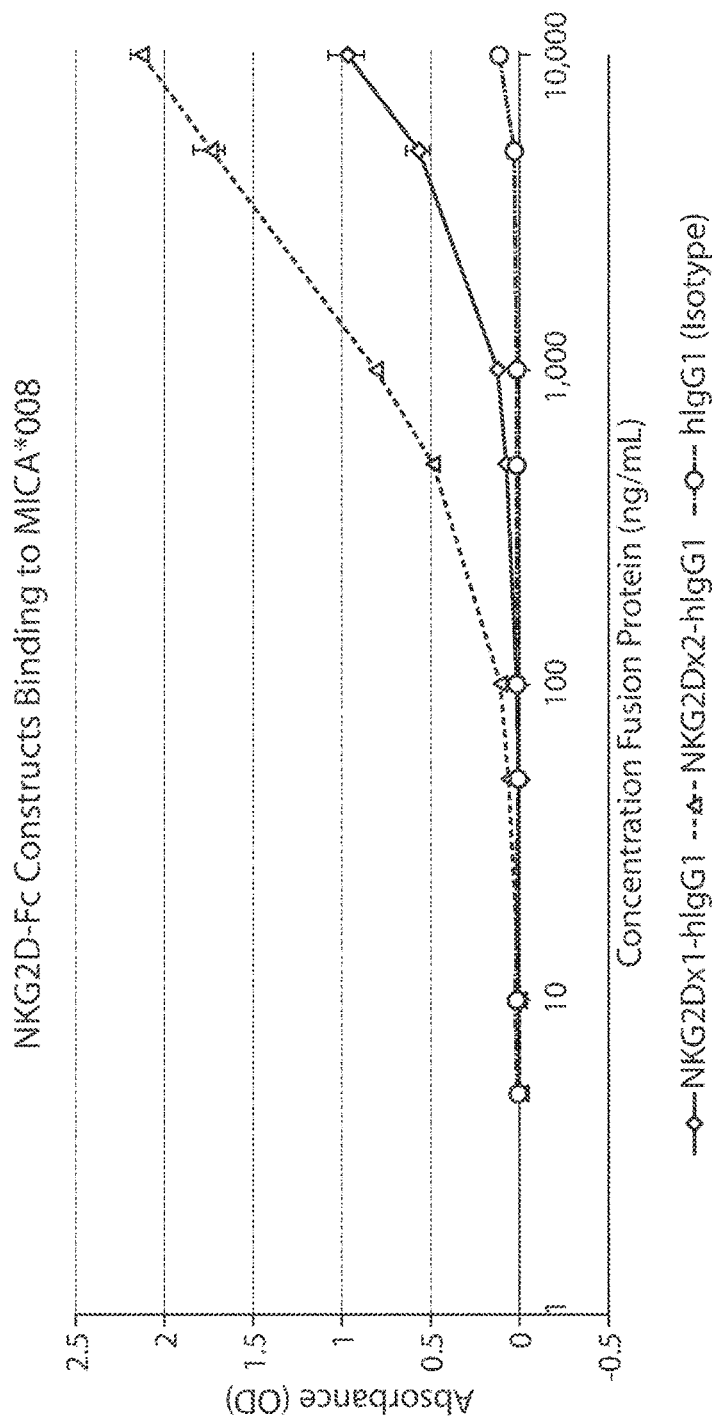
FIG. 8 shows ELISA analysis demonstrating that NKG2Dx2-hIgG1 binds to MICA*008 with improved avidity as compared to hNKG2Dx1-hIgG1, which is monomeric NKG2D-Fc chimera.
Figure 9:
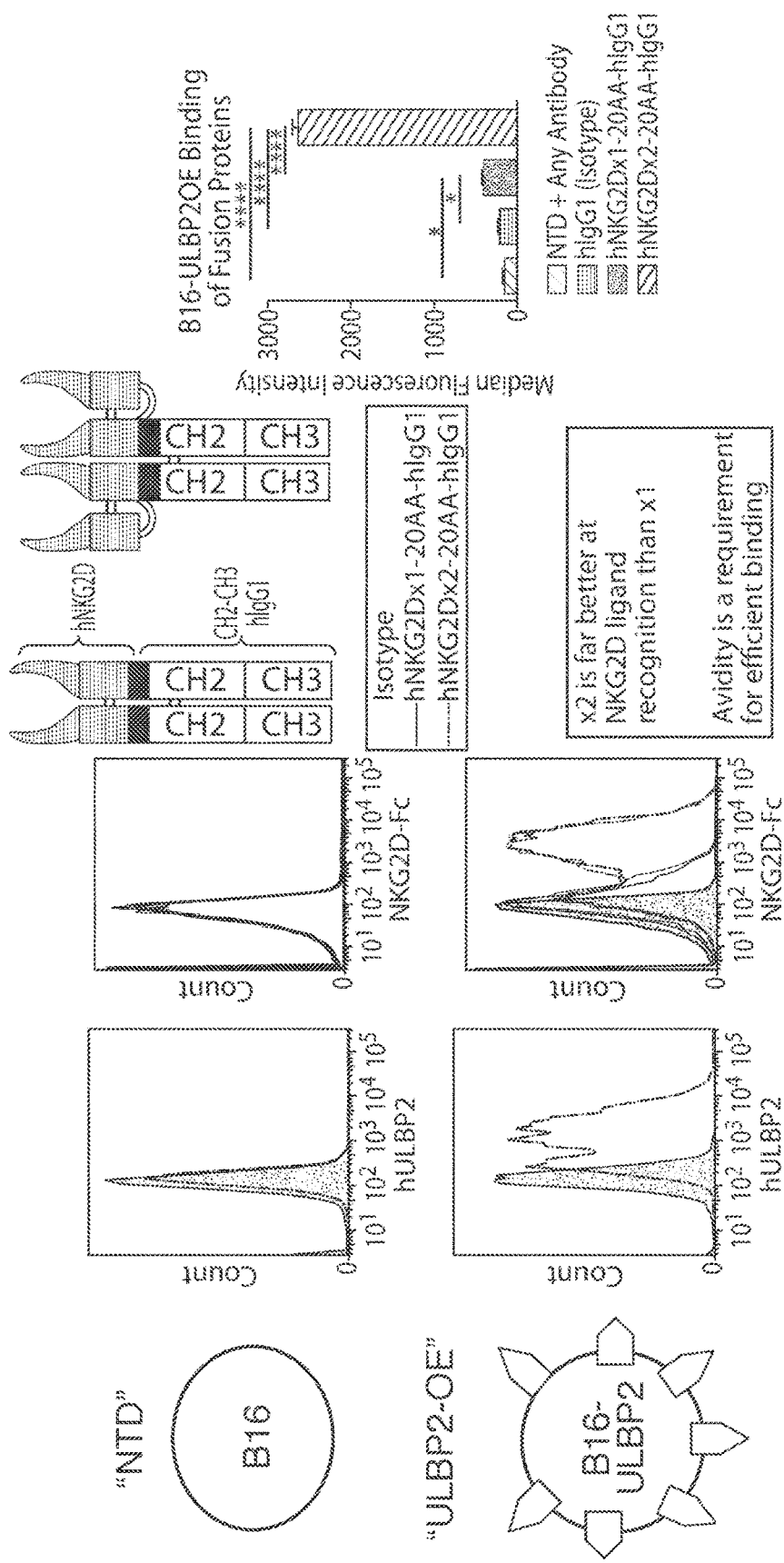
FIG. 9 shows flow cytometry analysis demonstrating that hNKG2Dx2-hIgG1 binds with improved avidity to NKG2D ligand-expressing cells as compared to hNKG2Dx1-hIgG1.
Figure 13:
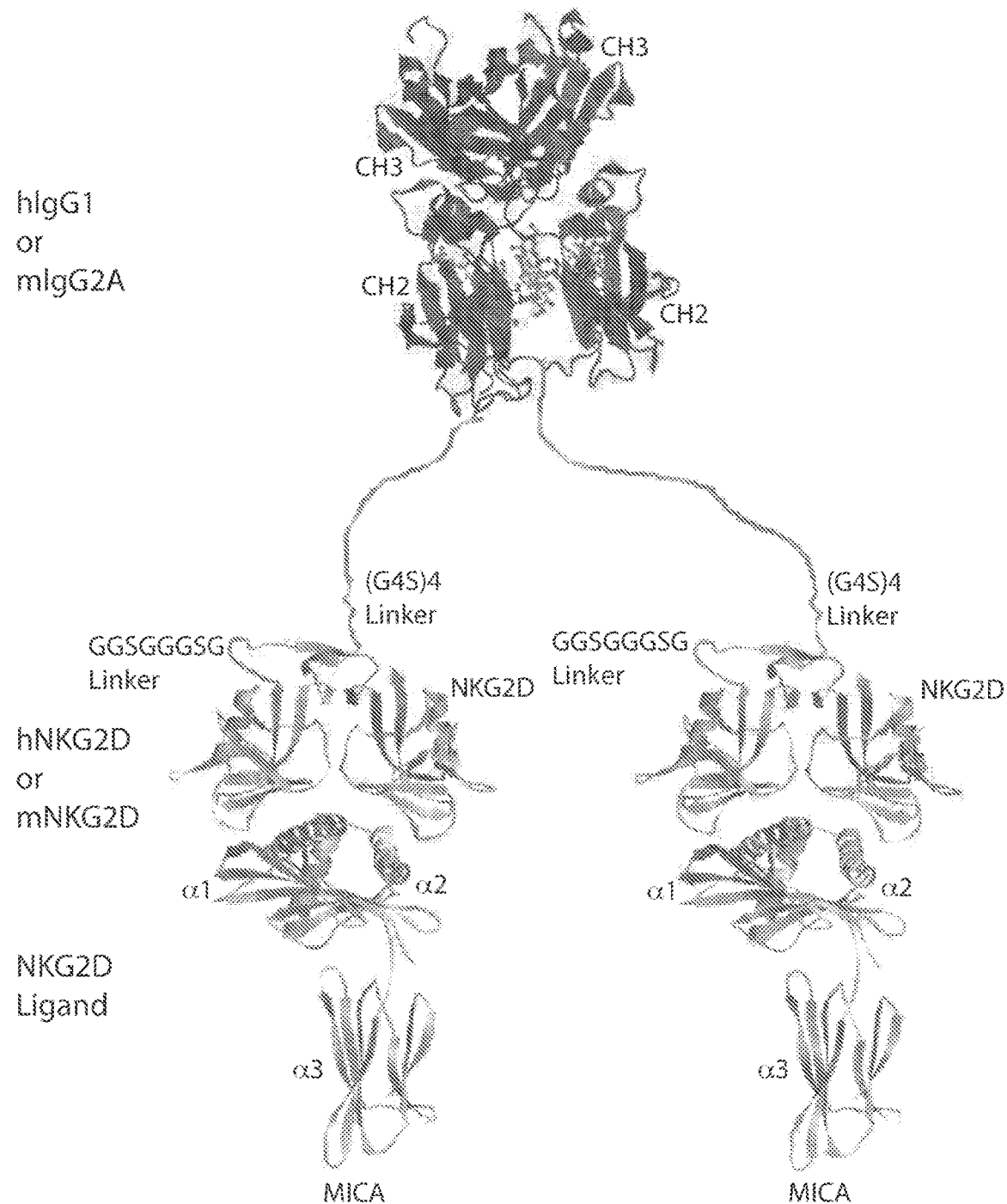
FIG. 13 shows a structural model of dimeric hNKG2D-hIgG1 in complex with human MICA (hMICA). $(G_4S)_4$ is SEQ ID NO: 3; GGSGGGSG is SEQ ID NO: 5.

A protein model showing NKG2Dx2-hIgG1 in complex with the NKG2D ligand MICA is shown in FIG. 13. Binding of NKG2Dx2-hIgG1 and hNKG2Dx1-hIgG1 constructs to MICA*008 was assayed by ELISA and flow cytometry. FIG. 8 shows ELISA data demonstrating that NKG2Dx2-hIgG1 binds to MICA*008 with improved avidity as compared to hNKG2Dx1-hIgG1. FIG. 9 depicts flow cytometry data showing that hNKG2Dx2-hIgG1 binds with improved avidity to NKG2D ligand-expressing cells as compared to hNKG2Dx1-hIgG1.

Figure 10:
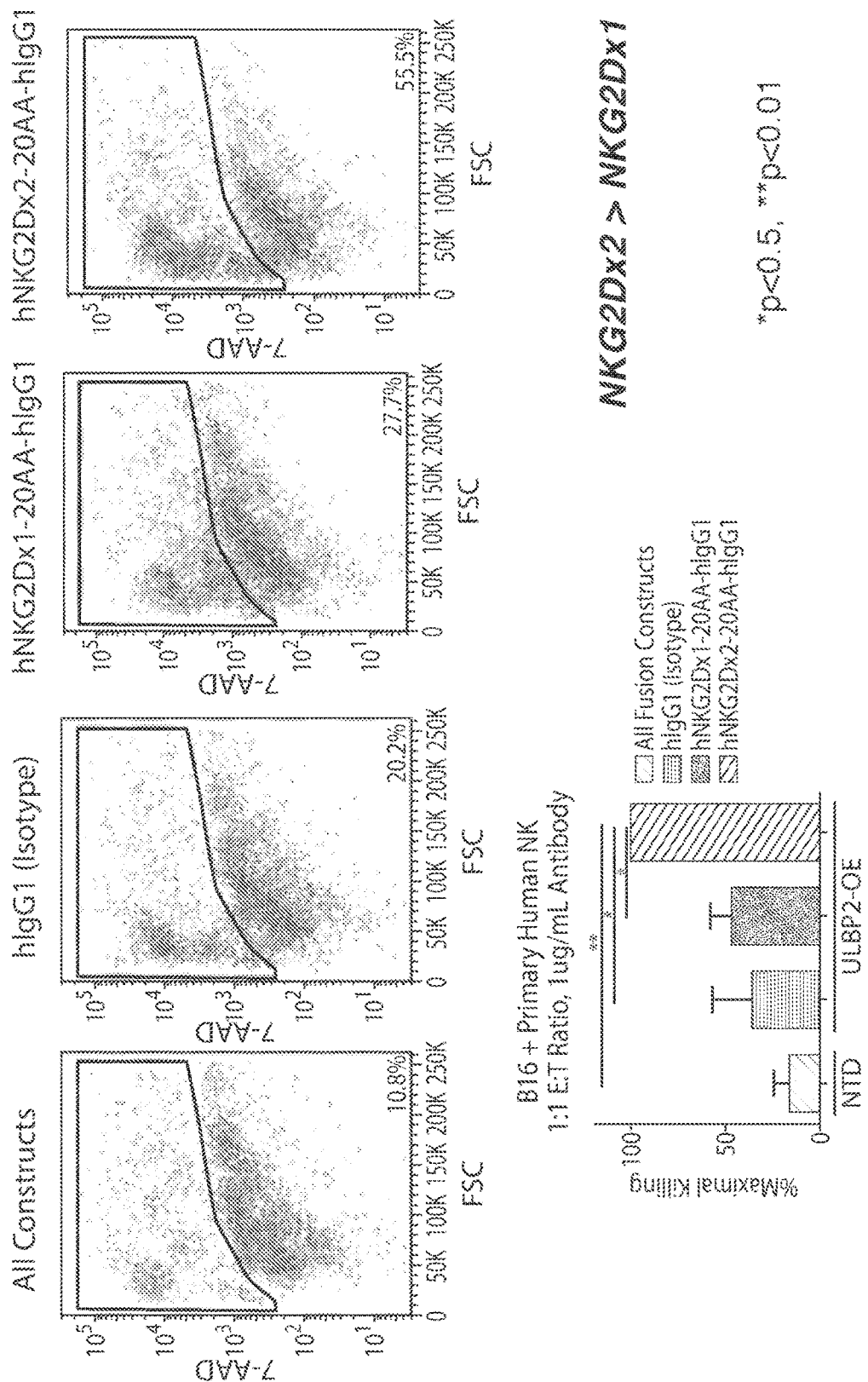
FIG. 10 shows NKG2D-Fc drives NK cell killing of ligand-positive targets. Dimeric NKG2D-Fc chimeras are more effective in mediating killing than monomeric NKG2D-Fc chimeras. * depicts $p<0.5$, and ** depicts $p<0.01$.

FIG. 10 shows NKG2D-Fc drives NK cell killing of ligand-positive (e.g., NKG2D ligand expressing) targets. In particular, hNKG2Dx2-20AA-hIgG1 mediated significantly higher killing of B16 cells than hNKG2Dx1-20AA-hIgG1.

Figure 11:
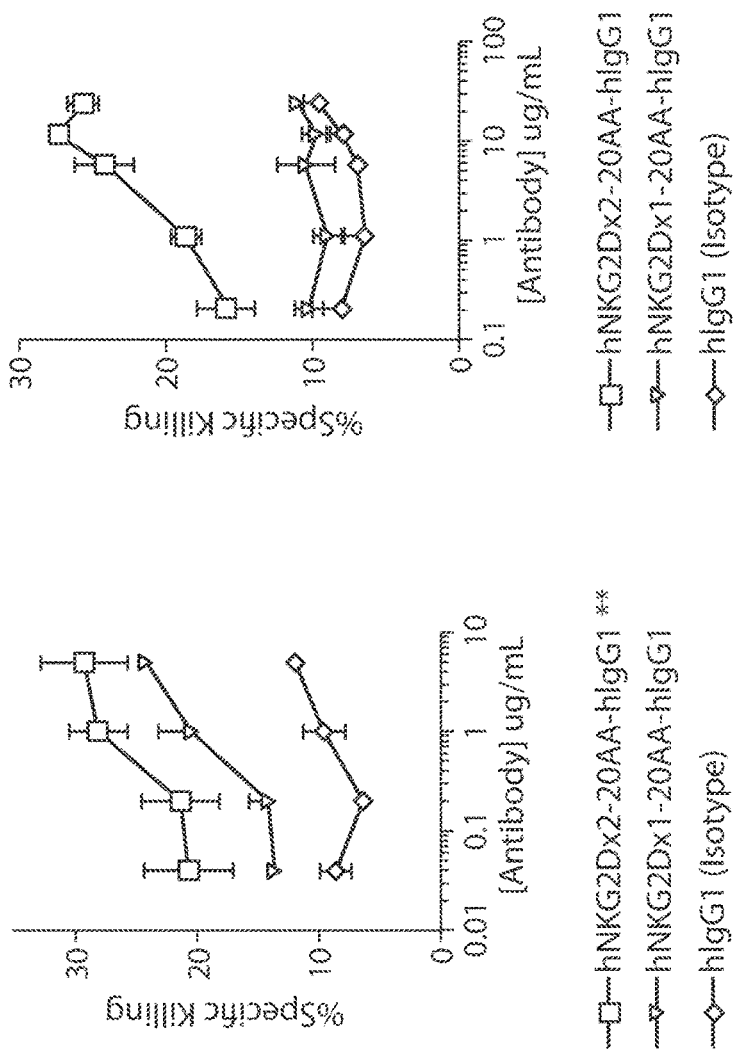
FIG. 11 shows dimeric NKG2D-Fc chimeras (e.g., hNKG2Dx2-hIgG1) kill NKG2D ligand-expressing cells more efficiently than monomeric NKG2D-Fc chimeras (e.g., hNKG2Dx1-hIgG1). ** depicts $p<0.01$.

FIG. 11 shows hNKG2Dx2-hIgG1 improves killing of NKG2D ligand-expressing cells as compared to hNKG2Dx1-hIgG1. B16-ULBP20E and HeyA8 cells were tested.

Tumors can shed their NKG2D ligands, which further impairs the immune response. One potential solution to this issue is to "sponge up" soluble NKG2D ligands (e.g., soluble MICA) to restore immune system function. FIG. 12 shows NKG2Dx2-hIgG1 neutralization of soluble MICA is superior to NKG2Dx1-hIgG1.

EQUIVALENTS

Those skilled in the art will recognize, or be able to ascertain using no more than routine experimentation, many equivalents of the specific embodiments of the invention described herein. Such equivalents are intended to be encompassed by the following claims.

---

What is claimed is:

1. A method of treating an NKG2D ligand expressing cancer, comprising administering to a subject in need thereof a polypeptide chain comprising:
   (a) a first ligand binding fragment of human NKG2D;
   (b) a second ligand binding fragment of human NKG2D; and
   (c) an Fc domain of a human immunoglobulin comprising:
      (i) a CH2 domain; and
      (ii) a CH3 domain.

2. The method of claim 1, wherein the first and second ligand binding fragments each comprise an extracellular fragment of the NKG2D receptor.

3. The method of claim 2, wherein the first and second ligand binding fragments are identical.

4. The method of claim 2, wherein the first and second ligand binding fragments are different.

5. The method of claim 1, wherein the human immunoglobulin is an IgG1.

6. The method of claim 1, wherein the polypeptide chain comprises a linker between the first and second ligand binding fragments.

7. The method of claim 6, wherein the linker is a flexible peptide linker.

8. The method of claim 7, wherein the linker comprises two or more of the following amino acids: glycine, serine, alanine, and threonine.

9. The method of claim 7, wherein the linker is 25 or fewer amino acids in length.

10. The method of claim 7, wherein the linker is 20 or fewer amino acids in length.

11. The method of claim 7, wherein the linker is 12 or fewer amino acids in length.

12. The method of claim 1, wherein the Fc domain of the polypeptide chain further comprises a hinge domain.

13. The method of claim 1, wherein the polypeptide chain does not comprise a cytokine.

14. The method of claim 1, wherein the polypeptide chain does not comprise a drug moiety.

15. The method of claim 1, wherein the polypeptide chain administered is in the form of a homodimer comprising two individual polypeptide chains dimerized through their respective Fc domains.

16. The method of claim 1, wherein the NKG2D ligand expressing cancer is melanoma, lung cancer, plasma cell cancer, leukemia, lymphoma, ovarian cancer, colon cancer, pancreatic cancer or prostate cancer.

17. The method of claim 15, wherein the NKG2D ligand expressing cancer is melanoma, lung cancer, plasma cell cancer, leukemia, lymphoma, ovarian cancer, colon cancer, pancreatic cancer or prostate cancer.

* * * * *